(12) United States Patent
Blyth et al.

(10) Patent No.: US 12,370,216 B2
(45) Date of Patent: *Jul. 29, 2025

(54) CANCER-KILLING CELLS

(71) Applicant: LIfT BioSciences Ltd, Brighton (GB)

(72) Inventors: Alex Blyth, Brighton (GB); Nico Bruyniks, Brighton (GB)

(73) Assignee: LIft BioSciences Ltd, Brighton (GB)

( * ) Notice: Subject to any disclaimer, the term of this patent is extended or adjusted under 35 U.S.C. 154(b) by 91 days.

This patent is subject to a terminal disclaimer.

(21) Appl. No.: 18/189,826

(22) Filed: Mar. 24, 2023

(65) Prior Publication Data

US 2023/0346834 A1 Nov. 2, 2023

Related U.S. Application Data

(63) Continuation of application No. 16/345,366, filed as application No. PCT/GB2017/053222 on Oct. 25, 2017, now Pat. No. 11,642,373.

(30) Foreign Application Priority Data

Oct. 26, 2016 (GB) .................................... 1618106

(51) Int. Cl.

| | | |
|---|---|---|
| *A61K 35/15* | (2025.01) | |
| *A61K 31/198* | (2006.01) | |
| *A61K 31/202* | (2006.01) | |
| *A61K 31/375* | (2006.01) | |
| *A61K 31/59* | (2006.01) | |
| *A61K 35/28* | (2015.01) | |
| *A61K 38/19* | (2006.01) | |
| *A61K 38/20* | (2006.01) | |
| *A61K 38/27* | (2006.01) | |
| *A61K 40/10* | (2025.01) | |
| *A61K 40/42* | (2025.01) | |
| *A61P 35/00* | (2006.01) | |
| *C12N 5/0787* | (2010.01) | |
| *C12N 5/0789* | (2010.01) | |
| *G01N 33/574* | (2006.01) | |

(52) U.S. Cl.
CPC ............ *A61K 35/15* (2013.01); *A61K 31/198* (2013.01); *A61K 31/202* (2013.01); *A61K 31/375* (2013.01); *A61K 31/59* (2013.01); *A61K 35/28* (2013.01); *A61K 38/193* (2013.01); *A61K 38/20* (2013.01); *A61K 38/27* (2013.01); *A61K 40/10* (2025.01); *A61K 40/42* (2025.01); *A61P 35/00* (2018.01); *C12N 5/0642* (2013.01); *C12N 5/0647* (2013.01); *G01N 33/57438* (2013.01); *A61K 2239/31* (2023.05); *A61K 2239/38* (2023.05); *A61K 2239/54* (2023.05); *C12N 2500/32* (2013.01); *C12N 2500/38* (2013.01); *C12N 2501/02* (2013.01); *C12N 2501/145* (2013.01); *C12N 2501/22* (2013.01); *C12N 2501/2303* (2013.01); *C12N 2501/2304* (2013.01); *C12N 2501/2306* (2013.01); *C12N 2501/2308* (2013.01); *C12N 2501/2318* (2013.01); *C12N 2501/25* (2013.01); *C12N 2501/26* (2013.01); *C12N 2501/305* (2013.01); *C12N 2501/825* (2013.01); *C12N 2506/11* (2013.01); *C12N 2506/45* (2013.01)

(58) Field of Classification Search
None
See application file for complete search history.

(56) References Cited

U.S. PATENT DOCUMENTS

| | | |
|---|---|---|
| 5,639,599 A | 6/1997 | Ryder et al. |
| 5,733,541 A | 3/1998 | Taichman |
| 5,811,301 A | 9/1998 | Cameron |
| 6,010,697 A | 1/2000 | Smith |
| 2003/0235909 A1 | 12/2003 | Hariri |
| 2006/0222625 A1 | 10/2006 | Brown |
| 2008/0089875 A1 | 4/2008 | Cui et al. |
| 2014/0072545 A1 | 3/2014 | Verneris |
| 2019/0314409 A1 | 10/2019 | Blyth et al. |
| 2021/0189340 A1 | 6/2021 | Blyth et al. |
| 2023/0203441 A1 | 6/2023 | Blyth |
| 2024/0197776 A1 | 6/2024 | Blyth et al. |
| 2024/0285681 A1 | 8/2024 | Blyth |

FOREIGN PATENT DOCUMENTS

| | | |
|---|---|---|
| CN | 103215340 A | 7/2013 |
| CN | 110755449 A | 2/2020 |
| RU | 2603079 C2 | 3/2015 |
| WO | WO199318648 A1 | 9/1993 |
| WO | WO1995010291 A1 | 4/1995 |
| WO | WO2002038189 | 5/2002 |
| WO | WO2003087392 A2 | 10/2003 |
| WO | WO2004020613 A1 | 3/2004 |
| WO | WO2005041891 A2 | 5/2005 |

(Continued)

OTHER PUBLICATIONS

US 2023/0011510 A1, 01/2023, Blyth (withdrawn)
Anklesaria, et al., "Studies on Electrophoretic Mobility of Leukocytes from Chronic Myeloid Leukemia Patients," Indian J. Experim. Biol., vol. 23, No. 11, 1985, 4 pages.
Bass, et al., "Comparison of human eosinophils from normals and patients with eosinophilia," J Clin. Invest., vol. 66, No. 6, 1980, pp. 1265-1273.
Bitmansour, et al., "Myeloid progenitors protect against invasive aspergillosis and seudomonas aeruginosa infection following hematopoietic stem cell transplantation", Blood, vol. 100, No. 13, 2002, pp. 4660-4667.
Boyum, "Isolation of Lymphocytes, Granulocytes and Macrophages", Srnad. J. Immunol., vol. 5, Suppl. 5, 1976, pp. 9-15.

(Continued)

*Primary Examiner* — Daniel C Gamett
(74) *Attorney, Agent, or Firm* — Lee & Hayes, P.C.

(57) ABSTRACT

The present invention relates to an in vitro culture of haematopoietic cells, wherein said haematopoietic cells differentiate to form granulocytes characterised by the ability to kill cancer cells. The invention also relates to said granulocytes, methods for identifying said haematopoietic cells and granulocytes, compositions and kits comprising the same, as well as uses of the same for treating cancer.

18 Claims, 2 Drawing Sheets

(56) References Cited

FOREIGN PATENT DOCUMENTS

| WO | WO2008011664    | 1/2008  |
|----|-----------------|---------|
| WO | WO2008045528 A2 | 4/2008  |
| WO | WO2010100570 A2 | 9/2010  |
| WO | WO2011088402 A2 | 7/2011  |
| WO | WO1992015322 A1 | 9/2012  |
| WO | WO2017161001 A1 | 9/2017  |
| WO | WO2019147187 A1 | 8/2019  |
| WO | WO2021116713 A1 | 6/2021  |

OTHER PUBLICATIONS

Cameron, et al., "A comparison of the cytotoxic potential in polymorphonuclear leukocytes obtained from normal donors and cancer patients", Clin. Immunol. Immunopathol., vol. 28, No. 1, 1983, pp. 115-124.

Chen, et al., "Targeting Negative Surface Charges of Cancel Cells by Multifunctional Nanoprobes," Theranostics, vol. 6, No. 11, 2016, 12 pages.

Office Action Dated May 13, 2022 in European Application No. 18720346.8, 4 pages.

Fritze & Wendt, "About the influence of heparin on neutrophilic granulocytes," Klin. Wochenschr., vol. 33, 1955, pp. 719-722 (see p. 5 of Written Opinion of the Intl. Prelim. Exam. Auth. Dated Jan. 30, 2019).

Gallin, et al., "Degranulating stimuli decrease the neagative surface charge and increase the adhesiveness of human neutrophils," J. Clin. Invest., vol. 65, No. 2, 1980, pp. 298-306.

Search Report Dated Jul. 28, 2020 in Great Britain Application No. GB1918313.6, 5 pages.

Search Report Dated Jul. 28, 2020 in Great Britain Application No. GB1918341.7, 4 pages.

International Preliminary Report on Patentability Dated Feb. 23, 2022 in International Application No. PCT/GB2020/053199, 25 pages.

International Preliminary Report on Patentability Dated Feb. 11, 2020 in International Application No. PCT/GB2018/051073.

Office Action Dated Jan. 5, 2022 in Japanese Application No. 2020-543405, 7 pages.

Office Action Dated Sep. 27, 2022 in Japanese Application No. 2020-543405, 12 pages.

Kyriazis, et al., "Human Pancreatic Adenocarcinoma Line Capan-1 in Tissue Culture and the Nude Mouse", Am. J. Patol., vol. 106, No. 2, 1982, pp. 250-260.

Lachmann, et al., "Large-Scale Hematopoietic Differentiation of Human Induced Pluripotent Stem Cells Provides Granulocytes or Macrophages for Cell Replacement", Stem Cell Reports, vol. 4, 2015, pp. 282-296.

Lee, et al., "CAP37, a neutrophil-derived inflammatory mediator, augments leukocyte adhesion to endothelial monolayers", Microvascular Res., vol. 66, No. 1, 2003, pp. 38-48.

Lichtman, et al., "Alteration of the Cell Periphery During Granulocyte Maturation: Relationship to Cell Function", Blood, vol. 39, No. 3, 1972, pp. 301-316.

Lim, et al., "Hemeatopoietic cell differentiation from embryonic and induced pluripotent stem cells", Stem Cell Research & Therapy, vol. 4, No. 71, 2013, 11 pages.

Lyons, et al., "Immune cell profiling in cancer: molecular approaches to cell-specific identification," NPJ Precis. Oncol., vol. 1, No. 1, 2017, 8 pages.

Neely, et al., "Flagellin Treatment Prevents Increased Susceptibility to Systemic Bacterial Infection after Injury by Inhibiting Anti-Inflammatory IL-10+ IL-12-Neutrophil Polarization", PLoS One, vol. 9, No. 1, 2014, 10 pages.

Office Action Dated Mar. 10, 2023 for U.S. Appl. No. 16/759,293, 23 pages.

Office Action Dated Oct. 19, 2022 for U.S. Appl. No. 16/759,293, 25 Pages.

Office Action Dated Jun. 17, 2022 for U.S. Appl. No. 16/345,366, 7 pages.

Peters, "Granulocyte transfusions in neutropenic patients: beneficial effects proven?" Vox Songuinis, vol. 91, 2009, pp. 275-283.

Shaul, et al., "Tumor-associated neutrophils display a distinct N1 profile following TGF(beta] modulation: A transcriptomics analysis of pro- vs. antitumor TANs", Oncoimmunology, vol. 5, No. 11, 2016, 14 pages.

Search Report Dated Aug. 14, 2017 in GB Application No. 1618106. 7, 5 pages.

Search Report and Written Opinion Dated Jan. 2, 2018 in International Application No. PCT/GB2017/053222, 14 pages.

Search Report & Written Opinion Dated Mar. 16, 2021 in International Application No. PCT/GB2020/053197, 21 pages.

Search Report and Written Opinion Dated May 11, 2021 in International Application No. PCT/GB2020/053199, 21 pages.

Tate, et al., "The role of neutrophils in the upper and lower respiratory tract during influenza virus infection of mice," Respir. Res., vol. 9, No. 1, 2008, 13 pages.

Timmins, et al., "Clinical scale ex vivo manufacture of neutrophils from hematopoietic progenitor cells," Biotechnol. Bioeng., vol. 104, No. 4, 2009, pp. 832-840.

Trump, et al., "Neutrophils Derived from Genetically Modified Human Induced Pluripotent Stem Cells Circulate and Phagocytose Bacteria In Vivo", Stem Cells Transl. Med., vol. 8, No. 6, 21 2019, pp. 556-567.

Written Opinion of the Intl. Prelim. Exam. Auth. Dated Jan. 30, 2019 in Application No. PCT/GB2017/053222, 5 pages.

Written Opinion Dated Oct. 29, 2021 in International Application No. PCT/GB2020/053197, 11 pages.

Written Opinion Dated Oct. 29, 2021 in International Application No. PCT/GB2020/053199, 10 pages.

Written Opinion Dated Sep. 24, 2019 in International Application No. PCT/GB2018/051073, 6 pages.

Yan, et al., "Human polymorphonuclear neutrophils specifically recognize and ki lls cancerous cells," Oncoimmunol., vol. 3, No. 7, 2014, 9 pages.

Yavuz, et al., "Differential expression of toll-like receptor 6 on granulocytes and monocytes implicates the role of microorganisms in Behcet's disease etiopathogenesis," Rheumatol. Int., vol. 28, No. 5, 2007, pp. 401-406.

Caux, et al., "Tumor Necrosis Factor-alpha Strongly Potentiates Inerleukin-3 and Granulocyte-Macrophage Colony-Stimulating Factor-Induced Proliferation of Human CD34+ Hematopoietic Progenitor Cells", Blood, vol. 75, No. 12, Jun. 15, 1990, 7 pages.

Clausen, et al., "Suppression of Natural Killer Cells in the Presence of CD34+ Blood Progenitor Cells and Peripheral Blood Lymphocytes", Biology of Blood and Marrow Transplantation, vol. 10, Jun. 15, 2004, 7 pages.

Office Action Dated Jan. 4, 2024 for Chinese Application No. 201880069094.4, 19 pages.

Fiedler, et al., "The role of transcription factors in the guidance of granulopoiesis", Am. J. Blood Res., vol. 2, No. 1, 2012, 9 pages.

Frey, "Influence of Silver Nanoparticle Surface Charge on Cytotoxic Efficacy against Cancer Cells," Cal Poly, College of Engineering, 2017, 33 pages.

Horzum, et al., "CD66b+ monocytes represent a proinflammatory myeloid subpopulation in cancer", Cancer Immunology, Immunotherapy, vol. 70, Jul. 6, 2020, 13 pages.

Ito, et al., CD62L expression level determines the cell fate of myeloid progenitors, Stem Cell Reports, vol. 16, Dec. 14, 2021, 16 pages.

Kreisel, et al., "Emergency granulopoiesis promotes neutrophil-dendritic cell encounters that prevent mouse lung allograft acceptance", Blood, vol. 118, No. 23, Dec. 1, 2011, 12 pages.

Marini, et al., "Mature CD10+ and immature CD10− neutrophils present in G-CSF-treated donors display opposite effects on T cells", Blood, vol. 129, No. 10, Mar. 9, 2017, 14 pages.

Tabbara MD, et al., "Allogeneic Hematopoietic Stem Cell Transplantation", Arch. Intern. Med., vol. 162, Jul. 22, 2022, 9 pages.

Yanez et al., "Granulocyte-Monocyte Progenitors and Monocyte-Dendritic Cell Progenitors Independently Produce Functionally Distinct Monocytes", Immunity, vol. 47, Nov. 21, 2017, 18pp.

(56) References Cited

OTHER PUBLICATIONS

Chinese Office Action Dated Feb. 27, 2023 for Chinese Application No. 201880069094.4, 8 pages.
Lichtman, & Weed, "Electrophoretic mobility and N-acetyl neuraminic acid content of human normal and leukemic lymphocytes and granulocytes", Blood, vol. 35, No. 1, 1970, pp. 12-22.
Kao, et al., "Efficacy verification and microscopic observations of an anticancer peptide, CB1a, on single lung cancer cell," Biochimica et Biophysica Acta, No. 1818, 2012, pp. 2927-2935.
Russian Office Action Dated Oct. 24, 2024 in Russian Application No. 2022115634, 13 pages.

CANCER-KILLING CELLS

CROSS-REFERENCE TO RELATED APPLICATIONS

This application is a continuation of U.S. patent application Ser. No. 16/345,366, filed on Apr. 26, 2019, which is a U.S. National Phase patent application based on International Patent Application No. PCT/GB2017/053222, filed on Oct. 25, 2017, which claims priority to Great Britain Patent Application No. 1618106.7, filed on Oct. 26, 2016, all of which are incorporated herein by reference in their entirety as if fully set forth herein.

The present invention relates to a cell-based therapy suitable for treating cancer.

Cancer is a leading cause of morbidity and mortality worldwide, with an annual increase in cancer incidence in developed countries. The World Health Organisation stated that in 2012 alone there were approximately 14 million new cancer cases (and 8.2 million associated deaths), with a projected rise to 22 million cases over the next two decades. Current therapeutic strategies include combinations of surgery, radiation, and cytotoxic chemotherapy, however many of these treatments are ultimately ineffective and associated with harmful side-effects.

Safety and efficacy has been assessed for Hematopoietic Stem Cell Transplantation (HSCT) as a therapeutic technique for treating certain cancers, such as Renal Cell Carcinoma. However, this treatment is still largely seen as experimental due to potentially fatal safety issues, with recipients exhibiting severe Graft vs. Host Disease (GVHD) as a result of the uncontrolled multiplication of pluripotent stem cells. Thus, there is a need for improved and alternative cancer therapies.

In spite of the increased cancer incidence, it has been observed that approximately 50-60% of individuals do not develop cancer in their lifetime. Indeed, in rare cases, some individuals exhibit spontaneous cancer regression. This observation has led to the study of white blood cells from spontaneous regressor individuals, and use of said white blood cells in Leukocyte Infusion Therapy (LIFT).

Conventional LIFT is carried out using apheresis for direct transfer of granulocytes (e.g. neutrophils) taken from the donor to the cancer patient. The current approach is not practical or scalable for use as a credible cancer therapeutic. First, granulocytes such as neutrophils have a very limited shelf-life (typically less than 24 hours) making them difficult to store. Secondly, apheresis requires approximately 5 (very rare) donors in order to acquire the required cell volume. Thirdly, to avoid an immune response from repeat exposure, the same donors cannot be used in a subsequent administration, thus requiring an increased pool of appropriate donors. Fourthly, it cannot be realistically expected that donors will be available on request, or willing to provide an endless source of granulocytes for the LIFT procedure. Fifthly, cancer killing efficacy of donor-derived granulocytes varies over time resulting in inconsistent therapeutic results.

As of yet, no viable alternative to conventional LIFT has been provided, nor has there been provided a solution to the associated problems. Thus, conventional LIFT is not viable as a scalable, safe, and reliable therapeutic technique.

The present invention provides a solution to at least one of the problems described above.

The present inventors have surprisingly found that it is possible to select for haematopoietic cells that are capable of differentiating into granulocytes having the ability to kill cancer cells. Once such a haematopoietic cell has been selected from a donor, said cell can be either stored for subsequent therapeutic purposes, or used directly as a medicament, for example in the treatment of cancer. Advantageously haematopoietic cells obtainable by a method of the invention can be immortalised thus providing a stable cell line that can be stored and/or propagated indefinitely. The present invention thus reduces the need for multiple rare donors, and/or for direct transfer of granulocytes collected from a donor to a cancer patient. Thus the invention provides a viable, scalable, safe and/or reliable therapy.

In one aspect the present invention provides an in vitro cell culture of haematopoietic cells, wherein said haematopoietic cells differentiate to form granulocytes characterised by:
  a. a surface potential defined by an electrophoretic mobility of at least 2.0 $\mu m \cdot cm/volt \cdot sec$ (or at least 1.0 $\mu m \cdot cm/volt \cdot sec$, for example at least 1.25 $\mu m \cdot cm/volt \cdot sec$, 1.5 $\mu m \cdot cm/volt \cdot sec$, or 1.75 $\mu m \cdot cm/volt \cdot sec$); and
  b. the ability to kill cancer cells.

In a related aspect the invention provides a method for selecting a haematopoietic cell suitable for use in treating cancer, said method comprising:
  a. measuring a surface potential of a granulocyte cell obtainable from a donor; and
  b. selecting a haematopoietic cell from said donor when the measured surface potential is defined by an electrophoretic mobility of at least 2.0 $\mu m \cdot cm/volt \cdot sec$ (or at least 1.0 $\mu m \cdot cm/volt \cdot sec$, for example at least 1.25 $\mu m \cdot cm/volt \cdot sec$, 1.5 $\mu m \cdot cm/volt \cdot sec$, or 1.75 $\mu m \cdot cm/volt \cdot sec$).

The term "obtainable" as used herein also encompasses the term "obtained".

The invention provides a method for selecting a haematopoietic cell comprising: measuring a surface potential of the haematopoietic cell; and selecting a haematopoietic cell that can be differentiated into a granulocyte that is suitable for treating cancer. Thus, in one aspect there is provided a method for selecting a haematopoietic cell suitable for use in treating cancer, said method comprising:
  a. measuring a surface potential of the haematopoietic cell; and
  b. selecting a haematopoietic cell that has a greater (e.g. more positive) surface potential than an otherwise identical haematopoietic cell that differentiates to form a granulocyte having a surface potential defined by an electrophoretic mobility of less than 2.0 $\mu m \cdot cm/volt \cdot sec$ (or less than 1.0 $\mu m \cdot cm/volt \cdot sec$) and/or has a reduced ability to kill cancer cells.

A related aspect provides use of a surface potential of a haematopoietic cell, for selecting a cell that can be differentiated into a granulocyte that is suitable for treating cancer, wherein the surface potential is greater (e.g. more positive) than the surface potential of an otherwise identical haematopoietic cell that differentiates to form a granulocyte having a surface potential defined by an electrophoretic mobility of less than 2.0 $\mu m \cdot cm/volt \cdot sec$ (or less than 1.0 $\mu m \cdot cm/volt \cdot sec$) and/or has a reduced ability to kill cancer cells.

The invention provides an in vitro method for selecting a subject for treatment (e.g. a subject that will benefit from a medicament described herein), said method comprising:
  a. admixing a granulocyte from said subject with a cancer cell line;
  b. incubating said admixture;
  c. measuring the % of cancer cells killed in said admixture; and d. selecting a subject for treatment with an in vitro cell culture of haematopoietic cells, or a granulocyte, or an in vitro cell culture of granulocytes, or a pharmaceutical composition of the invention, when the granulocyte from said subject kills less than 70% of the cancer cells in the admixture (suitably when the granulocyte from said subject kills less than 50%, preferably less than 25%, of the cancer cells in the admixture).

In some embodiments a subject is selected for treatment with an in vitro cell culture of haematopoietic cells, or a granulocyte, or an in vitro cell culture of granulocytes, or a pharmaceutical composition of the invention, when the granulocyte from said subject kills less than 20% or 10% of the cancer cells in the admixture. Preferably a subject is selected for treatment with an in vitro cell culture of haematopoietic cells, or a granulocyte, or an in vitro cell culture of granulocytes, or a pharmaceutical composition of the invention, when the granulocyte from said subject kills less than 5% or 1% of the cancer cells in the admixture.

The in vitro method may also be used to monitor the ability of a subject's granulocytes to kill cancer cells.

In one aspect the invention provides an in vitro method for selecting a granulocyte suitable for use in treating pancreatic cancer, said method comprising:
a. admixing a granulocyte with a pancreatic cancer cell line to form an admixture;
b. incubating said admixture;
c. measuring the % of pancreatic cancer cells killed in said admixture; and
d. selecting a granulocyte that kills at least 70% of the pancreatic cancer cells in the admixture.

The pancreatic cancer cell line may be a pancreatic ductal adenocarcinoma cell line.

A related aspect provides an in vitro method for selecting a granulocyte suitable for use in treating cancer, said method comprising:
a. admixing a granulocyte with a plurality of different cancer cell lines to provide a plurality of admixtures;
b. incubating said admixtures;
c. measuring the % of cancer cells killed in said admixtures; and
d. selecting a granulocyte as suitable for use in treating a cancer of the same type/subset as the cancer cell line, when said granulocyte kills at least 70% of the cancer cells in the admixture.

The foregoing in vitro methods may further comprise measuring and/or selecting a granulocyte based on a surface potential as disclosed herein. The foregoing in vitro methods may further comprise measuring and/or selecting a granulocyte based on cell density (e.g. of at least 1.077 g/ml) as disclosed herein. The foregoing in vitro methods may further comprise measuring and/or selecting a granulocyte based on the expression or activity of toll-like receptors; and/or an absence of expression or inactivity of: programmed death 1 (PD-1) receptor; CD115; CD224; CXCR1; and/or CXCR2 on said granulocyte.

Advantageously, such a method allows rapid screening of a granulocyte for the ability to kill multiple cancer types/subsets. In some embodiments the granulocyte is then catalogued according to the types/subsets of cancer that the granulocyte is suitable for use in treating.

The term "type" as used herein means cancer of the same organ or tissue as the cancer cell line. For example, if the cancer cell line is a pancreatic ductal adenocarcinoma cell line, then a granulocyte that kills at least 70% of pancreatic ductal adenocarcinoma cells in an admixture is considered to be suitable for use in treating all pancreatic cancers.

The term "subset" as used herein means not only that the cancer is of the same organ or tissue, but that the cancer shares additional characteristics with the cancer cell line (e.g. both are carcinomas, sarcomas, etc. of the same organ or tissue). For example if the cancer cell line is a pancreatic ductal adenocarcinoma cell line, then a granulocyte that kills at least 70% of pancreatic ductal adenocarcinoma cells in an admixture is considered to be suitable for use in treating all pancreatic ductal adenocarcinoma variants.

The in vitro methods according to the two foregoing aspects are representative of Cancer Killing Activity (CKA) assays.

The term "admix" as used herein means mixing one or more components together in any order, whether sequentially or simultaneously.

The term "plurality" means at least two. In one embodiment "plurality" means at least 3, 4, 5, 6, 7, 8, 9, 10, 11, 12, 13, 14, 15, 16, 17, 18, 19, or 20. "Plurality" may mean at least 30, 40, 50, 60, 70, 80, 90 or 100. In one embodiment "plurality" means 2, 3, 4, 5, 6, 7, 8, 9, 10, 11, 12, 13, 14, 15, 16, 17, 18, 19, or 20. In another embodiment "plurality" means 30, 40, 50, 60, 70, 80, 90 or 100.

In one embodiment the granulocyte is obtainable from a donor, for example a human donor. Alternatively or additionally the granulocyte may be obtainable from a subject having a cancer of a different type/subset to the cancer cell line(s) used in a method of the invention. Advantageously, the inventors have found that a subject having cancer of one type/subset may have granulocytes with the ability to kill cancer cells of a different cancer type/subset. This is surprising, especially when the subject has particularly low concentrations of granulocytes with the ability to kill cells of the cancer with which the subject has been diagnosed.

The cancer cell line may be one or more selected from a pancreatic cancer cell line, a liver cancer cell line, an oesophageal cancer cell line, a stomach cancer cell line, a cervical cancer cell line, an ovarian cancer cell line, a lung cancer cell line, a bladder cancer cell line, a kidney cancer cell line, a brain cancer cell line, a prostate cancer cell line, a myeloma cancer cell line, a non-Hodgkin's lymphoma (NHL) cell line, a larynx cancer cell line, a uterine cancer cell line, or a breast cancer cell line. In a preferable embodiment the cancer cell line is not a HeLa cell line.

Suitable cell lines are available commercially from the American Type Culture Collection United Kingdom (U.K.), Guernsey, Ireland, Jersey and Liechtenstein, LGC Standards, Queens Road, Teddington, Middlesex, TW11 OLY, UK. For example, a pancreatic cell line may be one or more of Capan-2, ATCC HTB-80; Panc 10.05, ATCC CRL-2547; CFPAC-1, ATCC CRL-1918; HPAF-II, ATCC CRL-1997; SW 1990, ATCC CRL-2172; BxPC-3, ATCC CRL-1687; AsPC-1, ATCC CRL-1682; ATCC® TCP-1026™; SW1990, ATCC CRL-2172; SU.86.86, ATCC CRL-1837; BXPC-3, ATCC CRL-1687; Panc 10.05, ATCC CRL-2547; MIA-PaCa-2, ATCC CRL-1420; PANC-1, ATCC CRL-1469; or ATCC® TCP-2060™.

The incubation step may be carried out for between 6 hours to 6 days. Suitably, the incubation step may be carried out for between 6 hours and 2 days, for example for between 12 hours to 36 hours, such as between 16 to 24 hours. In one embodiment the incubation step is carried out for 24 hours. The incubation step may be carried out at any temperature suitable for cell growth and viability, for example at a temperature between 35° C. to 42° C., suitably at 37 or 39° C. Preferably the incubation step is carried out at 37 or 39° C. for 24 hours. Preferably the incubation step is carried out for 16-24 hours at 30-40° C. (e.g. 37° C.).

The % of cancer cells killed can be measured by reference to the total number of starting cancer cells. The number of cancer cells killed can be measured using any suitable means, for example by viability staining (e.g. trypan blue staining), and microscopy, or using other automated means, for example by cell electronic sensing equipment, such as the RT-CES™ system available from ACEA Biosciences, Inc. (11585 Sorrento Valley Rd., Suite 103, San Diego, CA 92121, USA).

The admixture may comprise at least 100:1 or 75:1 granulocytes to cancer cells. Suitably, the admixture may comprise at least 50:1 or 25:1 granulocytes to cancer cells (preferably a ratio of 10:1 granulocytes to cancer cells). In a preferred embodiment the admixture comprises less than 10:1 granulocytes to cancer cells, such as 5:1 or fewer granulocytes to cancer cells. Preferably the admixture comprises 1:1 or fewer granulocytes to cancer cells.

In one embodiment the admixture comprises $8 \times 10^5$ granulocytes and $1.5 \times 10^4$ cancer cells, or preferably $8 \times 10^5$ granulocytes and $8 \times 10^4$ cancer cells.

Suitably, a granulocyte may be selected if it kills at least 80%, 85%, 90% or 95% of the cancer cells. Granulocytes that kill less than 70% (suitably less than 80%, 85%, 90% or 95%) of the cancer cells are preferably discarded.

In one embodiment an in vitro method for selecting a granulocyte suitable for use in treating cancer comprises:
a. admixing a granulocyte with a cancer cell line (preferably a pancreatic cancer cell line or a plurality of different cancer cell lines) to provide an admixture (or plurality of admixtures), wherein each admixture comprises $8 \times 10^5$ granulocytes, and $8 \times 10^4$ cancer cells;
b. incubating said admixture (or admixtures) at 39° C. for 24 hours;
c. measuring the % of cancer cells killed in said admixture (or admixtures); and
d. selecting a granulocyte as suitable for use in treating a cancer of the same type/subset as the cancer cell line, when said granulocyte kills at least 70% of the cancer cells in the admixture.

In one embodiment an in vitro method according to the foregoing aspects may also comprise parallel assaying of the granulocytes of a subject to be treated.

An in vitro method according to the present invention may further comprise obtaining a haematopoietic cell from a donor from whom the selected granulocyte is obtainable or has been obtained. Thus, the in vitro methods of the invention may also constitute methods for selecting a haematopoietic cell suitable for use in treating cancer.

In one aspect the invention provides an in vitro method for selecting a haematopoietic cell suitable for use in treating cancer (e.g. pancreatic cancer), said method comprising:
a. admixing a granulocyte obtainable from a donor with a cell line (e.g. a pancreatic cancer cell line) to form an admixture;
b. incubating said admixture;
c. measuring the % of cancer cells (e.g. pancreatic cancer cells) killed in said admixture; and
d. selecting a haematopoietic cell from said donor when said granulocyte kills at least 70% of the cancer cells (e.g. pancreatic cancer cells) in the admixture.

In another embodiment an in vitro method for selecting a haematopoietic cell suitable for use in treating cancer comprises:
a. admixing a granulocyte obtainable from a donor with a plurality of different cancer cell lines to provide a plurality of admixtures;
b. incubating said admixtures;
c. measuring the % of cancer cells killed in said admixtures; and
d. selecting a haematopoietic cell from said donor as suitable for use in treating a cancer of the same type/subset as the cancer cell line killed by said granulocyte when said granulocyte kills at least 70% of the cancer cells in the admixture.

The in vitro method may further comprise measuring and/or selecting a haematopoietic cell based on a surface potential as disclosed herein and/or based on a surface potential of a granulocyte differentiated therefrom. The in vitro method may further comprise measuring and/or selecting a haematopoietic cell based on cell density (e.g. of at least 1.077 g/ml) as disclosed herein and/or based on a cell density (e.g. of at least 1.077 g/ml) of a granulocyte differentiated therefrom. The in vitro method may further comprise measuring and/or selecting a haematopoietic cell based on the expression or activity of toll-like receptors; and/or an absence of expression or inactivity of: programmed death 1 (PD-1) receptor; CD115; CD224; CXCR1; and/or CXCR2 on a granulocyte differentiated therefrom.

In one aspect there is provided a granulocyte obtainable (e.g. obtained) by an in vitro method of the invention.

Although the in vitro methods described herein typically rely upon: selecting a haematopoietic cell from a donor when a granulocyte kills at least 70% of cancer cells in the assay; or selecting a granulocyte when said granulocyte kills at least 70% of cancer cells in the assay; in some embodiments a haematopoietic cell or granulocyte may be selected when less than 70% of cancer cells are killed. In one embodiment a haematopoietic cell or granulocyte may be selected when a granulocyte kills at least 2%, 5%, 10%, 15%, 20%, 25%, 30%, 35%, 40%, 45%, 50%, 55%, 60% or 65% of cancer cells in the assay.

Therefore the term "kills at least 70%" as used herein may be replaced with kills at least 2%.

The term "kills at least 70%" as used herein may be replaced with kills at least 5% or 10%.

The term "kills at least 70%" as used herein may be replaced with kills at least 15% or 20%.

The term "kills at least 70%" as used herein may be replaced with kills at least 25% or 30%.

The term "kills at least 70%" as used herein may be replaced with kills at least 35% or 40%.

The term "kills at least 70%" as used herein may be replaced with kills at least 45% or 50%.

The term "kills at least 70%" as used herein may be replaced with kills at least 55% or 60%.

The term "kills at least 70%" as used herein may be replaced with kills at least 65%.

In such embodiments, granulocytes that kill less than 2%, 5%, 10%, 15%, 20%, 25%, 30%, 35%, 40%, 45%, 50%, 55%, 60% or 65% of cancer cells may be discarded.

The in vitro methods of the invention may comprise a combination of the techniques described herein to improve selection of cells suitable for treating cancer. For example, if multiple haematopoietic cells or granulocytes are selected because they meet the stipulated density threshold, cell surface potential/electrophoretic mobility may be assessed to help identify haematopoietic cells that produce high CKA granulocytes (e.g. neutrophils) or to select those granulocytes having improved CKA. Advantageously such a combination of techniques improves the ability to select haematopoietic cells or granulocytes of the invention. Moreover, by applying a combination of such techniques on granulocytes (e.g. neutrophils), cells with improved CKA may be detected, and haematopoietic cells obtained from said donors.

The invention also provides a differentiation method, said method comprising differentiating an in vitro cell culture of haematopoietic cells of the invention, or haematopoietic cells obtainable according to a method of the invention into granulocytes. In a related aspect there is provided an in vitro cell culture of granulocytes obtainable (e.g. obtained) by such a method. In one embodiment the in vitro cell culture is enriched with granulocytes having:
 a. a surface potential defined by an electrophoretic mobility of at least 2.0 µm·cm/volt·sec (or at least 1.0 µm·cm/volt·sec, for example at least 1.25 µm·cm/volt·sec, 1.5 µm·cm/volt·sec, or 1.75 µm·cm/volt·sec); and
 b. the ability to kill cancer cells.

In one aspect the invention provides a pharmaceutical composition comprising: a haematopoietic cell; and a granulocyte-macrophage colony-stimulating factor (GM-CSF), a granulocyte colony-stimulating factor (G-CSF), a growth hormone; serotonin, vitamin C, vitamin D, glutamine (Gln), arachidonic acid, AGE-albumin, an interleukin, TNF-alpha, Flt-3 ligand, thrombopoietin, foetal bovine serum (FBS), or combinations thereof.

In one embodiment a pharmaceutical composition comprises a haematopoietic cell; and a granulocyte-macrophage colony-stimulating factor (GM-CSF), and a granulocyte colony-stimulating factor (G-CSF), and a growth hormone, and serotonin, and vitamin C, and vitamin D, and glutamine (Gln), and arachidonic acid, and AGE-albumin, and an interleukin, and TNF-alpha, and Flt-3 ligand, and thrombopoietin, and foetal bovine serum (FBS).

Suitably a growth hormone may be a human growth hormone. The haematopoietic cell comprised in the composition may be obtainable (e.g. obtained) by a method of the present invention, or may be part of an in vitro cell culture of haematopoietic cells of the invention.

In one aspect the invention provides a pharmaceutical composition comprising: a granulocyte cell; a granulocyte-macrophage colony-stimulating factor (GM-CSF), a granulocyte colony-stimulating factor (G-CSF), a growth hormone; serotonin, vitamin C, vitamin D, glutamine (Gln), arachidonic acid, AGE-albumin, an interleukin, TNF-alpha, Flt-3 ligand, thrombopoietin, foetal bovine serum (FBS), or combinations thereof. The granulocyte cell comprised in the composition may be obtainable (e.g. obtained) by a method of the present invention.

In one embodiment a pharmaceutical composition comprises a granulocyte cell; and a granulocyte-macrophage colony-stimulating factor (GM-CSF), and a granulocyte colony-stimulating factor (G-CSF), and a growth hormone, and serotonin, and vitamin C, and vitamin D, and glutamine (Gln), and arachidonic acid, and AGE-albumin, and an interleukin, and TNF-alpha, and Flt-3 ligand, and thrombopoietin, and foetal bovine serum (FBS).

An interleukin may be interleukin-3 (IL-3), interleukin 8 (IL-8), Interleukin-4 (IL-4), Interleukin-6 (IL-6), interleukin-18 (IL-18), or combinations thereof. Suitably an interleukin may be interleukin-3 (IL-3), interleukin 8 (IL-8), Interleukin-4 (IL-4), Interleukin-6 (IL-6), and interleukin-18 (IL-18).

In one embodiment a granulocyte-macrophage colony-stimulating factor (GM-CSF), granulocyte colony-stimulating factor (G-CSF), growth hormone, serotonin, AGE-albumin, interleukin, TNF-alpha, Flt-3 ligand, or thrombopoietin may be a human granulocyte-macrophage colony-stimulating factor (GM-CSF), granulocyte colony-stimulating factor (G-CSF), growth hormone, serotonin, AGE-albumin, interleukin, TNF-alpha, Flt-3 ligand, or thrombopoietin.

All of the above reagents are commercially available from Sino Biological Inc. (Suite B-310 (also Suite B-209, B-203), 14 Zhong He Street, BDA, Beijing 100176, P.R. China).

The invention also relates to an in vitro cell culture of haematopoietic cells, a granulocyte, an in vitro cell culture of granulocytes, or a pharmaceutical composition described herein for use as a medicament. The medicament may be for use in treating cancer, thus in a related aspect there is provided an in vitro cell culture of haematopoietic cells, a granulocyte, an in vitro cell culture of granulocytes, or a pharmaceutical composition for use in treating cancer. A corresponding method for treating cancer is also provided comprising administering to a subject in need thereof an in vitro cell culture of haematopoietic cells, a granulocyte, an in vitro cell culture of granulocytes, or a pharmaceutical composition.

In another aspect the invention provides a cell bank comprising an in vitro cell culture of haematopoietic cells, a granulocyte, an in vitro cell culture of granulocytes, or a pharmaceutical composition of the invention.

In a further aspect there is provided a kit comprising:
 a. an in vitro cell culture of haematopoietic cells, a granulocyte, an in vitro cell culture of granulocytes, or a pharmaceutical composition of the invention; and
 b. instructions for use of same in medicine.

The term "haematopoietic cell" as used herein refers to a cell of the hematopoiesis pathway that is capable of differentiating into a granulocyte (preferably a neutrophil). The term "haematopoietic cell" thus encompasses a haematopoietic stem cell, as well as a precursor cell differentiated from a haematopoietic stem cell, wherein said precursor cell is capable of differentiating into a granulocyte (preferably a neutrophil). The precursor cell may be referred to herein as a "granulocyte precursor cell". A haematopoietic cell in accordance with the present invention may relate to a haematopoietic stem cell, a granulocyte precursor cell or combinations thereof. The term "haematopoietic cell" as used herein does not encompass a human embryonic stem cell.

In one embodiment a haematopoietic cell is a haematopoietic stem cell. A haematopoietic stem cell can be selected on the basis of cell surface polypeptide markers, for example selected from CD34, CD59, Thy1, CD38, C-kit, and lin. In one embodiment a haematopoietic stem cell comprises the cell surface polypeptide markers $CD34^+$, $CD59^+$, $Thy1^+$, $CD38^{low/-}$, $C\text{-}kit^{low/-}$, and $lin^-$. Preferably a haematopoietic cell expresses CD34.

In another embodiment a haematopoietic cell is a granulocyte precursor cell. A granulocyte precursor cell may be one or more selected from a common myeloid progenitor cell, a myeloblast, a N. promyelocyte, a N. myelocyte, a N. metamyelocyte, a N. band, or combinations thereof.

A haematopoietic cell (such as a haematopoietic stem cell or a granulocyte precursor cell) or cell culture may be differentiated into a granulocyte. Differentiation may be carried out using any suitable method, such as a method based on the disclosure in Lieber et al, Blood, 2004 Feb. 1; 103(3):852-9, and/or Choi et al, Nat. Protoc., 2011 March; 6(3):296-313, which are incorporated herein by reference.

In one aspect the invention provides a method of differentiating a haematopoietic cell comprising admixing said haematopoietic cell with a granulocyte-macrophage colony-stimulating factor (GM-CSF), a granulocyte colony-stimulating factor (G-CSF), a growth hormone; serotonin, vitamin C, vitamin D, glutamine (Gln), arachidonic acid, AGE-albumin, an interleukin, TNF-alpha, Flt-3 ligand, thrombopoietin, foetal bovine serum (FBS), or combinations thereof.

In one embodiment the invention provides a method of differentiating a haematopoietic cell comprising admixing said haematopoietic cell with a granulocyte-macrophage colony-stimulating factor (GM-CSF), and a granulocyte colony-stimulating factor (G-CSF), and a growth hormone, and serotonin, and vitamin C, and vitamin D, and glutamine (Gln), and arachidonic acid, and AGE-albumin, and an interleukin, and TNF-alpha, and Flt-3 ligand, and thrombopoietin, and foetal bovine serum (FBS).

Said haematopoietic cell may be part of a haematopoietic cell culture.

In one embodiment differentiation of a haematopoietic cell comprises culturing said haematopoietic cell with one or more feeder cell(s). Suitably, a feeder cell may be an OP9 cell. OP9 cells (ATCC® CRL-2749™) are commercially available from the American Type Culture Collection United Kingdom (U.K.), Guernsey, Ireland, Jersey and Liechtenstein, LGC Standards, Queens Road, Teddington, Middlesex, TW11 0LY, UK. In one embodiment a haematopoietic cell may be cultured with one or more feeder cell(s) and Flt-3 ligand, thrombopoietin, fetal bovine serum (FBS), or combinations thereof.

Thus in one embodiment, a pharmaceutical composition or cell culture of the invention may further comprise a feeder cell, such as an OP9 cell.

The term "granulocyte" encompasses the following cell types: neutrophils, basophils, and eosinophils. Preferably the granulocyte is a neutrophil. A granulocyte may express the cell surface polypeptide markers CD11b and CD15. A granulocyte may also produce reactive oxygen species ($O_2^-$).

The present invention encompasses granulocytes that are suitable for use in treating cancer. Suitably, said granulocytes comprise a surface potential defined by an electrophoretic mobility of at least 2.0 µm·cm/volt·sec (suitably at least 2.25 µm·cm/volt·sec or at least 2.5 µm·cm/volt·sec). In one embodiment said granulocytes comprise a surface potential defined by an electrophoretic mobility of at least 2.75 µm·cm/volt·sec, or at least 3.0 µm·cm/volt·sec. Suitably, said granulocytes may comprise a surface potential defined by an electrophoretic mobility of at least 3.25 µm·cm/volt·sec, or at least 3.5 µm·cm/volt·sec. Preferably said granulocytes may comprise a surface potential defined by an electrophoretic mobility of at least 3.75 µm·cm/volt·sec, or at least 4.0 µm·cm/volt·sec. The granulocytes also have the ability to kill cancer cells.

Alternatively, said granulocytes may comprise a surface potential defined by an electrophoretic mobility of at least 1.0 µm·cm/volt·sec or at least 1.25 µm·cm/volt·sec. For example, said granulocytes may comprise a surface potential defined by an electrophoretic mobility of at least 1.5 µm·cm/volt·sec, or at least 1.75 µm·cm/volt·sec. The granulocytes also have the ability to kill cancer cells.

The "ability to kill cancer cells" can be determined by admixing a cell (e.g. a granulocyte, such as a neutrophil) with a cancer cell, and measuring (e.g. after incubation) viability of said cancer cell. If the cancer cell is no longer viable (i.e. has been killed), the cell exhibits an ability to kill cancer cells. In one embodiment the ability to kill cancer cells is determined using a Cancer Killing Activity (CKA) assay described herein.

In a preferable embodiment a CKA assay comprises:
a. admixing a granulocyte with a cancer cell line to provide an admixture, wherein said admixture comprises $8\times10^5$ granulocytes, and $8\times10^4$ cancer cells;
b. incubating said admixture at 39° C. for 24 hours;
c. measuring the % of cancer cells killed in said admixture.

In a preferable embodiment a CKA assay comprises:
a. admixing a granulocyte with a cancer cell line to provide an admixture, wherein said admixture comprises at least 1:1 (e.g. 5:1 or 10:1) granulocytes to cancer cells;
b. incubating said admixture for 16-24 hours (e.g. at 30-40° C.);
c. measuring the % of cancer cells killed in said admixture.

A cell with the ability to kill cancer cells may be defined as a cell that has at least 70% or 75% CKA in a CKA assay herein (e.g. the CKA assay above). Suitably, said cell may have at least 80% or 90% activity in a CKA assay herein (e.g. the CKA assay above).

A cell with the "ability to kill cancer cells" is suitable for use in treating cancer. Haematopoietic cells that can be differentiated into cells with the "ability to kill cancer cells" are also considered to be suitable for use in treating cancer.

In one aspect the invention provides an in vitro cell culture of haematopoietic cells, wherein said haematopoietic cells differentiate to form granulocytes characterised by:
a. a density of at least 1.077 g/ml; and
b. the ability to kill cancer cells.

A granulocyte having a density of at least 1.077 g/ml may be obtainable by a method described in Example 11. In one embodiment such a method comprises:
i. providing a sucrose solution adjusted to a density of 1.077 g/ml;
ii. adding a composition comprising granulocytes; and
iii. centrifuging to pellet high-density granulocytes (e.g. neutrophils).

A granulocyte having a density of at least 1.077 g/ml may be obtainable using a commercially available kit, such as the Histopaque®-1077 kit (commercially available from Sigma-Aldrich, Catalogue No. 10771-100ML).

In some embodiments a granulocyte having a density of 1.077 g/ml is obtained by Ficoll-Paque separation. Typically such granulocytes are found in the bottom of a 1.077 Ficoll-Paque medium following separation, while lower density granulocytes (e.g. having a density of less than 1.077 g/ml) are found at the 1.077-plasma interface.

Thus, a granulocyte according to (and for use in) the present invention may have a density of at least 1.077 g/ml, and granulocytes having a density of less than 1.077 g/ml may be excluded from the present invention. In some embodiments, a granulocyte according to the invention has a density of at least 1.077 g/ml and a cell surface potential described herein. Therefore, all of the cell surface potential embodiments apply equally to said granulocytes.

Preferably the granulocyte has a density greater than 1.077 g/ml.

In one embodiment a granulocyte has a density of at least 1.078 g/ml. In one embodiment a granulocyte has a density of at least 1.079 g/ml. In one embodiment a granulocyte has a density of at least 1.080 g/ml. In one embodiment a granulocyte has a density of at least 1.081 g/ml. In one embodiment a granulocyte has a density of at least 1.082 g/ml. In one embodiment a granulocyte has a density of at least 1.083 g/ml.

In one embodiment a granulocyte has a density of less than 1.084 g/ml. In one embodiment a granulocyte has a density of less than 1.083 g/ml. In one embodiment a granulocyte has a density of less than 1.082 g/ml. In one embodiment a granulocyte has a density of less than 1.081 g/ml. In one embodiment a granulocyte has a density of less than 1.080 g/ml. In one embodiment a granulocyte has a density of less than 1.079 g/ml. In one embodiment a granulocyte has a density of less than 1.078 g/ml.

In one embodiment a granulocyte has a density of 1.077 g/ml to 1.084 g/ml (e.g. a density greater than 1.077 g/ml but less than 1.084 g/ml). The granulocyte may have a density of 1.079 g/ml to 1.084 g/ml, for example a density of 1.080 g/ml to 1.084 g/ml. The granulocyte may have a density of 1.080 g/ml to 1.083 g/ml, for example a density of 1.080 g/ml to 1.082 g/ml.

In one embodiment a haematopoietic cell has a density of at least 1.077 g/ml. Preferably the haematopoietic cell has a density greater than 1.077 g/ml.

In one embodiment a haematopoietic cell has a density of at least 1.078 g/ml. In one embodiment a haematopoietic cell has a density of at least 1.079 g/ml. In one embodiment a haematopoietic cell has a density of at least 1.080 g/ml. In one embodiment a haematopoietic cell has a density of at least 1.081 g/ml. In one embodiment a haematopoietic cell has a density of at least 1.082 g/ml. In one embodiment a haematopoietic cell has a density of at least 1.083 g/ml.

In one embodiment a haematopoietic cell has a density of less than 1.084 g/ml. In one embodiment a haematopoietic cell has a density of less than 1.083 g/ml. In one embodiment a haematopoietic cell has a density of less than 1.082 g/ml. In one embodiment a haematopoietic cell has a density of less than 1.081 g/ml. In one embodiment a haematopoietic cell has a density of less than 1.080 g/ml. In one embodiment a haematopoietic cell has a density of less than 1.079 g/ml. In one embodiment a haematopoietic cell has a density of less than 1.078 g/ml.

In one embodiment a haematopoietic cell has a density of 1.077 g/ml to 1.084 g/ml (e.g. a density greater than 1.077 g/ml but less than 1.084 g/ml). The haematopoietic cell may have a density of 1.079 g/ml to 1.084 g/ml, for example a density of 1.080 g/ml to 1.084 g/ml. The haematopoietic cell may have a density of 1.080 g/ml to 1.083 g/ml, for example a density of 1.080 g/ml to 1.082 g/ml.

In one aspect the invention provides a method for selecting a haematopoietic cell suitable for use in treating cancer, said method comprising:
 a. measuring the density of a granulocyte cell obtainable from a donor; and
 b. selecting a haematopoietic cell from said donor when the measured density of the granulocyte is at least 1.077 g/ml.

The invention also provides a method for selecting a haematopoietic cell suitable for use in treating cancer, said method comprising:
 a. measuring the density of a haematopoietic cell; and
 b. selecting a haematopoietic cell that has a density greater than an otherwise identical haematopoietic cell that differentiates to form a granulocyte having a density of less than 1.077 g/ml and/or has a reduced ability to kill cancer cells In one aspect there is provided a method comprising differentiating an in vitro cell culture of haematopoietic cells, wherein said haematopoietic cells differentiate to form granulocytes characterised by:
 a. a density of at least 1.077 g/ml; and
 b. the ability to kill cancer cells.

The invention also provides an in vitro culture of granulocytes obtainable by the foregoing method.

In one aspect the invention provides an in vitro cell culture of haematopoietic cells, wherein said haematopoietic cells differentiate to form granulocytes characterised by:
 a. expression or activity of toll-like receptors; and/or an absence of expression or inactivity of: programmed death 1 (PD-1) receptor; CD115; CD224; CXCR1; and/or CXCR2; and
 b. the ability to kill cancer cells.

The presence or absence of said receptors may be determined using any techniques known to the person skilled in the art. For example, the skilled person may use a labelled antibody optionally in combination with FACS to detect the presence or absence of said receptors.

Receptor activity/inactivity may also be determined using any known technique. For example, by detecting changes in gene expression associated with said activity/inactivity.

Preferably the granulocytes express toll-like receptors; and do not express programmed death 1 (PD-1) receptor; CD115; CD224; CXCR1; and/or CXCR2 (preferably do not express programmed death 1 (PD-1) receptor; CD115; CD224; CXCR1; and CXCR2).

Alternatively or additionally, one or more of the PD-1 receptor; CD115; CD224; CXCR1; and CXCR2 may be expressed in an inactive form, or inactivated subsequent to expression.

The toll-like receptor may be one or more of: TLR1, TLR2, TLR3, TLR4, TLR5, TLR6, TLR7, TLR8, TLR9, TLR10, and/or TLR11. Preferably the toll-like receptor is TLR4.

Without wishing to be bound by theory, the inventors believe that:
 PD-L1 does not engage with its receptor PD-1 on granulocytes (e.g. neutrophils) with high CKA and/or that granulocytes (e.g. neutrophils) with high CKA do not produce PD-L1; and/or
 granulocytes (e.g. neutrophils) with high CKA have active toll-like receptors on their surface; and/or
 CD115 and CD224 markers are not expressed on granulocytes (e.g. neutrophils) with high CKA;
 CXCR1 and CXCR2 are receptors of granulocytes (e.g. neutrophils) with low CKA, i.e. granulocytes (e.g. neutrophils) with high CKA do not express CXCR1 & CXCR2, or CXCR1 and CXCR2 are inhibited in said granulocytes (e.g. neutrophils).

In one embodiment granulocytes having a cell surface polypeptide expression profile described above also have a cell surface potential and/or a density described herein.

In one aspect the invention provides a method for selecting a haematopoietic cell suitable for use in treating cancer, said method comprising:
 a. detecting the expression or activity of toll-like receptors; programmed death 1 (PD-1) receptor; CD115; CD224; CXCR1; and/or CXCR2 on a granulocyte cell obtainable from a donor; and
 b. selecting a haematopoietic cell from said donor when the toll-like receptors are expressed or activity; and/or programmed death 1 (PD-1) receptor; CD115; CD224; CXCR1; and/or CXCR2 are not expressed or inactive.

In one aspect there is provided a method comprising differentiating an in vitro cell culture of haematopoietic cells, wherein said haematopoietic cells differentiate to form granulocytes characterised by:

a. expression or activity of toll-like receptors; and/or an absence of expression or inactivity of: programmed death 1 (PD-1) receptor; CD115; CD224; CXCR1; and/or CXCR2; and
b. the ability to kill cancer cells.

The invention also provides an in vitro culture of granulocytes obtainable by the foregoing method.

A haematopoietic cell may be immortalised. The person skilled in the art is familiar with immortalisation techniques, which include inter alia introduction of a viral gene that deregulates the cell cycle (e.g. the adenovirus type 5 E1 gene), and artificial expression of telomerase. Immortalisation advantageously allows for the preparation of a cell line which can be stably cultured in vitro. Thus, in one aspect the invention provides an immortalised cell line obtainable (e.g. obtained) from a selected haematopoietic cell, as well as a stable haematopoietic cell culture. Suitably an immortalised cell line or stable haematopoietic cell culture is obtainable (e.g. obtained) by a method of the present invention.

The term "stable" as used in reference to a haematopoietic cell culture or cell line means that the cell culture or cell line has been modified such that it is more amenable to in vitro cell culture than an unmodified cell (i.e. a cell obtained from a donor and subjected directly to in vitro cell culture). Said "stable" cell culture or cell line is therefore capable of undergoing more rounds of replication (preferably for prolonged periods of time) when compared to an unmodified cell.

A haematopoietic cell is suitably obtainable (e.g. obtained) from a donor, for example a human donor.

The term "donor" as used herein refers to a subject (suitably a human subject) from whom a biofluid sample is obtained. Any suitable biofluid sample from which a haematopoietic cell or granulocyte cell is obtainable may be used in the present invention. In one embodiment a biofluid sample is a blood sample, such as a peripheral blood sample. The term "blood" as used herein encompasses whole blood, blood serum, and blood plasma. Blood may be subjected to centrifugation in order to separate red blood cells, white blood cells, and plasma. Following centrifugation, the mononuclear cell layer may be removed for use in the present invention.

The donor may be selected based on one or more of the following characteristics: sex, age, medical history, and/or blood group type. In one embodiment a donor may be selected if said donor is a male. In another embodiment a donor may be selected if said donor is aged 18-25 (suitably 18-24). Suitably, a donor may be selected if said donor is a male aged between 18-25 (suitably 18-24). Without wishing to be bound by theory, it is believed that males in early adulthood have a higher likelihood of producing granulocytes (e.g. neutrophils) having the ability to kill cancer cells.

Suitably granulocytes obtainable (e.g. obtained) from a donor may have a surface potential defined by an electrophoretic mobility of at least 2.0 μm·cm/volt·sec, and the ability to kill cancer cells. In another embodiment granulocytes obtainable (e.g. obtained) from a donor have a surface potential defined by an electrophoretic mobility of at least 1.0 μm·cm/volt·sec, and the ability to kill cancer cells.

The present invention relates to the measurement of cell surface potentials. A surface potential of a cell can be determined using any suitable technique known in the art. In one embodiment the surface potential is determined using electrophoresis. The electrophoresis technique may be carried out by applying a voltage to cells comprised within a suitable electrophoresis medium, and measuring cell mobility. The following protocol may be employed:

i. apply 200V direct current to cells (suspended in 10 mM Tris-HCl and 291 mM glucose buffer) comprised in an electrophoresis chamber; and
ii. measure the time taken for said cells (e.g. granulocytes or haematopoietic cells) to pass a fixed length while applying a current of 3 mA (e.g. via use of a microscope, optionally connected to a CCD camera).

Electrophoretic mobility "μ" (expressed in units μm·cm/volt·sec) can be calculated using the following formula:

$$\mu = ugS/I$$

wherein:
"u"=the electrophoretic velocity measured by step ii;
"g"=the conductivity of the electrophoresis medium;
"S"=the cross-sectional area of the electrophoresis chamber; and
"I"=the current.

In one embodiment electrophoretic mobility is determined by:
i. adding haematopoietic cells or granulocytes suspended in 10 mM Tris-HCl and 291 mM glucose to an electrophoresis chamber;
ii. applying 200V/3 mA direct current; and
iii. measuring the distance (mm) said haematopoietic cells or granulocytes travel in a given time towards the electrode; and
iv. calculating the electrophoretic mobility using the equation above.

The electrophoresis may be carried out in a 0.9% (isotonic) NaCl solution. Preferably a constant current is used (e.g. 3 mA).

An electrophoretic mobility assay may be one described in "Cell Electrophoresis" edited by Johann Bauer (ISBN 0-8493-8918-6 published by CRC Press, Inc.) the teaching of which is incorporated herein in its entirety.

Without wishing to be bound by theory, it is believed that haematopoietic cells (e.g. haematopoietic stem cells expressing CD34) that can differentiate into granulocytes (e.g. neutrophils) with higher CKA, are more positively charged and therefore travel further towards the negatively charged electrode in a given time than similar size and weight/density haematopoietic cells (e.g. haematopoietic stem cells expressing CD34) that differentiate into lower CKA granulocytes (e.g. neutrophils). Likewise, it is believed that granulocytes (e.g. neutrophils) with higher CKA, are more positively charged and therefore travel further towards the negatively charged electrode in a given time than similar size and weight/density granulocytes (e.g. neutrophils) that may have lower CKA.

The cell surface potential is equivalent to the electrophoretic mobility, and is proportional to the distance travelled by the cell in a given time during electrophoresis. A cell with a higher positive charge travels further towards the electrode during electrophoresis than a less positively-charged (or negatively-charged) cell. Such a cell will therefore have a greater cell surface potential value than a less positively-charged (or negatively-charged) cell. The surface potential of a cell may be defined by an electrophoretic mobility of at least 2.0 μm·cm/volt·sec or at least 2.25 μm·cm/volt·sec. Suitably the surface potential of a cell may be defined by an electrophoretic mobility of at least 2.5 μm·cm/volt·sec or at least 2.75 μm·cm/volt·sec. Suitably the surface potential of a cell may be defined by an electrophoretic mobility of at least 3.0 μm·cm/volt·sec or at least 3.25 μm·cm/volt·sec. Preferably the surface potential of a cell may be defined by an electrophoretic mobility of at least 3.5 μm·cm/volt·sec or at least 3.75 μm·cm/volt·sec. More preferably the surface potential of a cell may be defined by an electrophoretic mobility of at least 4.0 μm·cm/volt·sec. The cell may be a haematopoietic cell, or a granulocyte cell.

In one embodiment a haematopoietic cell of the invention may have a surface potential defined by an electrophoretic mobility of at least 1.0 μm·cm/volt·sec or at least 1.25 μm·cm/volt·sec, for example at least 1.5 μm·cm/volt·sec or 1.75 μm·cm/volt·sec (preferably at least 2.0 μm·cm/volt·sec). In one embodiment, a haematopoietic cell may have a surface potential defined by an electrophoretic mobility of at least 2.25 μm·cm/volt·sec or at least 2.5 μm·cm/volt·sec. Suitably, a haematopoietic cell may have a surface potential defined by an electrophoretic mobility of at least 2.75 μm·cm/volt·sec or at least 3.0 μm·cm/volt·sec. Preferably, a haematopoietic cell may have a surface potential defined by an electrophoretic mobility of at least 3.25 μm·cm/volt·sec or at least 3.5 μm·cm/volt·sec. More preferably, a haematopoietic cell may have a surface potential defined by an electrophoretic mobility of at least 3.75 μm·cm/volt·sec or at least 4.0 μm·cm/volt·sec.

In one embodiment a granulocyte cell of the invention may have a surface potential defined by an electrophoretic mobility of at least 1.0 μm·cm/volt·sec or at least 1.25 μm·cm/volt·sec, for example at least 1.5 μm·cm/volt·sec or at least 1.75 μm·cm/volt·sec (preferably at least 2.0 μm·cm/volt·sec). In one embodiment, a granulocyte cell may have a surface potential defined by an electrophoretic mobility of at least 2.25 μm·cm/volt·sec or at least 2.5 μm·cm/volt·sec. Suitably, a granulocyte cell may have a surface potential defined by an electrophoretic mobility of at least 2.75 μm·cm/volt·sec or at least 3.0 μm·cm/volt·sec. Preferably, a granulocyte cell may have a surface potential defined by an electrophoretic mobility of at least 3.25 μm·cm/volt·sec or at least 3.5 μm·cm/volt·sec. More preferably, a granulocyte cell may have a surface potential defined by an electrophoretic mobility of at least 3.75 μm·cm/volt·sec or at least 4.0 μm·cm/volt·sec.

The present invention comprises measuring the surface potential of granulocytes obtainable (e.g. obtained) from a donor. If the surface potential is defined by an electrophoretic mobility of at least 2.0 μm·cm/volt·sec (or alternatively at least 1.0 μm·cm/volt·sec), haematopoietic cells are selected from the donor. Advantageously, this provides a simple and/or quick and/or reliable screening method for the selection of haematopoietic cells suitable for use in treating cancer. In some embodiments by the employed method constitutes a quick screen can be used to determine if a donor is suitable, without the need for a more complex assay (such as a CKA assay). A functional assay (such as a CKA assay described herein) may be subsequently performed to validate the screening, for example by differentiating haematopoietic cells selected from a donor into granulocytes, and testing said granulocytes in a CKA assay. Cells that do not have the required cell surface potential and/or required CKA may be discarded.

Additionally or alternatively, a surface potential of a haematopoietic cell may be measured, and a haematopoietic cell selected if it has a greater surface potential than an otherwise identical haematopoietic cell that differentiates to form a granulocyte (e.g. a neutrophil) having a surface potential defined by an electrophoretic mobility of less than 2.0 μm·cm/volt·sec (preferably less than 2.5 μm·cm/volt·sec, more preferably less than 3.5 μm·cm/volt·sec or 4.0 μm·cm/volt·sec); and/or which has a reduced ability to kill cancer cells. Advantageously, this allows the rapid screening of haematopoietic cells to determine whether said cells are suitable for use in treating cancer. Thus, the invention encompasses haematopoietic cells having a greater surface potential than an otherwise identical haematopoietic cell that differentiates to form a granulocyte (e.g. a neutrophil) having a surface potential defined by an electrophoretic mobility of less than 2.0 μm·cm/volt·sec ((preferably less than 2.5 μm·cm/volt·sec, more preferably less than 3.5 μm·cm/volt·sec or 4.0 μm·cm/volt·sec); and/or which has a reduced ability to kill cancer cells.

In one embodiment haematopoietic cells that do not meet the screening criteria (e.g. that do not have a greater surface potential and/or which have a surface potential defined by an electrophoretic mobility of less than 2.0 μm·cm/volt·sec) are discarded.

Additionally or alternatively, a surface potential of a haematopoietic cell may be measured, and a haematopoietic cell selected if it has a greater surface potential than an otherwise identical haematopoietic cell that differentiates to form a granulocyte (e.g. a neutrophil) having a surface potential defined by an electrophoretic mobility of less than 1.0 μm·cm/volt·sec (suitably less than 1.25 μm·cm/volt·sec, more suitably less than 1.5 μm·cm/volt·sec or 1.75 μm·cm/volt·sec); and/or which has a reduced ability to kill cancer cells. Thus, the invention encompasses haematopoietic cells having a greater surface potential than an otherwise identical haematopoietic cell that differentiates to form a granulocyte (e.g. a neutrophil) having a surface potential defined by an electrophoretic mobility of less than 1.0 μm·cm/volt·sec (suitably less than 1.25 μm·cm/volt·sec, more suitably less than 1.5 μm·cm/volt·sec or 1.75 μm·cm/volt·sec); and/or which has a reduced ability to kill cancer cells.

In one embodiment haematopoietic cells that do not meet the screening criteria (e.g. that do not have a greater surface potential and/or which have a surface potential defined by an electrophoretic mobility of less than 1.0 μm·cm/volt·sec) are discarded.

The term "greater surface potential" means a more positive surface charge.

The "reduced ability to kill cancer cells" can be determined experimentally, by testing two or more granulocytes (e.g. neutrophils) under the same experimental conditions, and comparing the concentration/amount of cancer cells killed. The "reduced ability to kill cancer cells" may be determined using a CKA assay described herein. In one embodiment a "reduced ability to kill cancer cells" means that a cell kills 10% or 20% fewer cancer cells than cells of the invention (i.e. cells having the "ability to kill cancer cells" as defined herein).

Thus, following this method an appropriate haematopoietic cell surface potential value (allowing selection of haematopoietic cells that can be differentiated into granulocytes suitable for use in treating cancer) can be determined empirically, based on the correlation between the surface potential of granulocytes obtainable therefrom, and/or based on the ability to kill cancer cells.

In a related aspect the invention provides a method for selecting a haematopoietic cell suitable for use in treating cancer, said method comprising:
  a. measuring a surface potential of a haematopoietic cell obtainable from a donor, wherein a granulocyte (e.g. a neutrophil) obtainable from said donor is characterised by:
    i. a surface potential defined by an electrophoretic mobility of at least 2.0 μm·cm/volt·sec (or at least 1.0 μm·cm/volt·sec); and
    ii. the ability kill cancer cells; and
  b. using the measured surface potential in a method for selecting a haematopoietic cell.

The "method for selecting a haematopoietic cell" may refer to selecting a haematopoietic cell from the same donor from which the surface potential measurement has been obtained, or from a different donor.

A cell described herein may be part of a cell culture (e.g. an in vitro cell culture). The cell culture may comprise multiple different cell types (e.g. apart from the haematopoietic cell, or granulocyte cell).

In one embodiment the cell culture is an in vitro cell culture of haematopoietic cells. The cell culture may be enriched with haematopoietic cells that differentiate to form granulocytes characterised by a surface potential defined by an electrophoretic mobility of at least 2.0 μm·cm/volt·sec (or at least 1.0 μm·cm/volt·sec); and the ability to kill cancer cells. Alternatively or additionally, the cell culture may be enriched with haematopoietic cells that differentiate to form granulocytes having: a density of at least 1.077 g/ml; and the ability to kill cancer cells. Alternatively or additionally, the cell culture may be enriched with haematopoietic cells that differentiate to form granulocytes having expression or activity of toll-like receptors; and/or an absence of expression or inactivity of: programmed death 1 (PD-1) receptor; CD115; CD224; CXCR1; and/or CXCR2; and the ability to kill cancer cells.

The term "enriched with haematopoietic cells" means that haematopoietic cells that differentiate to form granulocytes characterised by:
  (i) a surface potential defined by an electrophoretic mobility of at least 2.0 μm·cm/volt·sec (or at least 1.0 μm·cm/volt·sec); or
  (ii) a density of at least 1.077 g/ml; or
  (iii) expression or activity of toll-like receptors; and/or an absence of expression or inactivity of: programmed death 1 (PD-1) receptor; CD115; CD224; CXCR1; and/or CXCR2; and
the ability to kill cancer cells, constitute at least 70%, 75%, 80%, 85%, 90% or 95% of the total haematopoietic cells (preferably total cells) comprised in the cell culture.

In another embodiment the cell culture is an in vitro cell culture of granulocytes. Said granulocytes are obtainable by differentiating a haematopoietic cell of the invention. The in vitro cell culture of granulocytes may be enriched with granulocytes having a surface potential defined by an electrophoretic mobility of at least 2.0 μm·cm/volt·sec (or at least 1.0 μm·cm/volt·sec); and the ability to kill cancer cells. Alternatively or additionally, the cell culture may be enriched with granulocytes having: a density of at least 1.077 g/ml; and the ability to kill cancer cells. Alternatively or additionally, the cell culture may be enriched with granulocytes having expression or activity of toll-like receptors; and/or an absence of expression or inactivity of: programmed death 1 (PD-1) receptor; CD115; CD224; CXCR1; and/or CXCR2; and the ability to kill cancer cells.

The term "enriched with granulocytes" means that granulocytes having:
  (i) a surface potential defined by an electrophoretic mobility of at least 2.0 μm·cm/volt·sec (or at least 1.0 μm·cm/volt·sec); or
  (ii) a density of at least 1.077 g/ml; or
  (iii) expression or activity of toll-like receptors; and/or an absence of expression or inactivity of: programmed death 1 (PD-1) receptor; CD115; CD224; CXCR1; and/or CXCR2; and
the ability to kill cancer cells, constitute at least 70%, 75%, 80%, 85%, 90% or 95% of the total granulocytes (preferably total cells) comprised in the cell culture.

A cell, cell culture or pharmaceutical composition of the invention may be subjected to one or more further processing steps, such as cryogenic freezing. The further processing step may include admixing said cell, cell culture or pharmaceutical composition with a preservation medium, for example a cryogenic preservation medium.

The invention may further comprise depositing a cell, cell culture, or pharmaceutical composition of the invention in a cell bank, and thus in a related aspect provides a cell bank comprising a cell, cell culture or pharmaceutical composition. The term "cell bank" as used herein refers to a storage facility which maintains a cell under suitable conditions for cell viability. For example, the cell may be stored in a metabolically dormant state (e.g. cryogenically frozen). Suitably, a cell comprised within a cell bank is catalogued for appropriate retrieval (e.g. based on blood group, and/or human leukocyte antigen (HLA) type). Where the cell bank is a granulocyte cell bank, said cell bank may be replenished using a haematopoietic cell of the invention.

A cell or cell culture of the invention may be formulated in any suitable manner, based on its downstream application (e.g. storage in a cell bank, or use in therapy).

In one embodiment a cell or cell culture of the invention is formulated as a pharmaceutical composition comprising a cell or cell culture of the invention, and a granulocyte-macrophage colony-stimulating factor (GM-CSF), a granulocyte colony-stimulating factor (G-CSF), a growth hormone; serotonin, vitamin C, vitamin D, glutamine (Gln), arachidonic acid, AGE-albumin, an interleukin, TNF-alpha, Flt-3 ligand, thrombopoietin, foetal bovine serum (FBS), or combinations thereof.

In one embodiment the cell culture of the invention is formulated as a pharmaceutical composition comprising a cell or cell culture of the invention, and a granulocyte-macrophage colony-stimulating factor (GM-CSF), and a granulocyte colony-stimulating factor (G-CSF), and a growth hormone, and serotonin, and vitamin C, and vitamin D, and glutamine (Gln), and arachidonic acid, and AGE-albumin, and an interleukin, and TNF-alpha, and Flt-3 ligand, and thrombopoietin, and foetal bovine serum (FBS).

In one embodiment a cell, cell culture or pharmaceutical composition is formulated with a pharmaceutically acceptable carrier. The term "pharmaceutically acceptable carrier" as used herein means a carrier that can be administered to a subject (e.g. a patient) intravenously, intra-arterially, intra-peritoneally, intra-tumourally, intrathecally or combinations thereof (preferably intravenously) without causing harm to said subject. Thus in one embodiment a pharmaceutically acceptable carrier is an injectable carrier, such as a sterile physiological saline solution.

The present invention provides cells, cell cultures and pharmaceutical compositions for use in medicine. For example, there is provided an in vitro cell culture of haematopoietic cells, a granulocyte, an in vitro cell culture of granulocytes, or a pharmaceutical composition of the invention for use as a medicament. The medicament is particularly useful in the treatment of cancer.

In one embodiment a cancer is a solid tumour cancer. The term "solid tumour cancer" refers to an abnormal, malignant mass of tissue that does not contain cysts or liquid inclusions. Examples of solid tumour cancers include carcinomas, sarcomas, and lymphomas.

A solid tumour cancer may be a carcinoma. A carcinoma may be selected from one or more of an adenocarcinoma, a basal cell carcinoma, a squamous cell carcinoma, an adenosquamous carcinoma, a renal cell carcinoma, a ductal carcinoma in situ (DCIS), an invasive ductal carcinoma, an anaplastic carcinoma, a large cell carcinoma, a small cell carcinoma or combinations thereof. A carcinoma may also be selected from epithelial neoplasms, squamous cell neoplasms, squamous cell carcinoma, basal cell neoplasms, basal cell carcinoma, transitional cell carcinomas, adenocarcinomas (such as Adenocarcinoma not otherwise specified (NOS), linitis plastica, vipoma, cholangiocarcinoma, hepatocellular carcinoma NOS, adenoid cystic carcinoma, renal cell carcinoma, Grawitz tumour), adnexal and skin appendage neoplasms, mucoepidermoid neoplasms, cystic mucinous and serous neoplasms, ductal lobular and medullary neoplasms, acinar cell neoplasms, or complex epithelial neoplasms.

Alternatively a solid tumour cancer may be a sarcoma. A sarcoma may be selected from Askin's tumour, sarcoma botryoides, chondrosarcoma, Ewing's, malignant hemangioendothelioma, malignant schwannoma, osteosarcoma, or soft tissue sarcomas (including alveolar soft part sarcoma, angiosarcoma, cystosarcoma phyllodes, dermatofibrosarcoma protuberans (DFSP), desmoid tumour, desmoplastic small round cell tumour, epithelioid sarcoma, extraskeletal chondrosarcoma, extraskeletal osteosarcoma, fibrosarcoma, gastrointestinal stromal tumour (GIST), hemangiopericytoma, hemangiosarcoma, Kaposi's sarcoma, leiomyosarcoma, liposarcoma, lymphangiosarcoma, malignant fibrous histiocytoma, undifferentiated pleomorphic sarcoma, malignant peripheral nerve sheath tumour (MPNST), neurofibrosarcoma, rhabdomyosarcoma, and synovial sarcoma).

Alternatively a solid tumour may be a lymphoma, such as a B-cell lymphoma, a T-cell lymphoma, a NK-cell lymphoma, or a Hodgkin's lymphoma.

In one embodiment an in vitro cell culture of haematopoietic cells, an in vitro cell culture of granulocytes, or a pharmaceutical composition of the invention is for use in treating one or more of: pancreatic cancer, liver cancer, oesophageal cancer, stomach cancer, cervical cancer, ovarian cancer, lung cancer, bladder cancer, kidney cancer, brain cancer, prostate cancer, myeloma cancer, non-Hodgkin's lymphoma (NHL), larynx cancer, uterine cancer, or breast cancer.

Preferably an in vitro cell culture of haematopoietic cells, an in vitro cell culture of granulocytes, or a pharmaceutical composition of the invention is for use in treating pancreatic cancer. The pancreatic cancer may be a pancreatic solid tumour cancer, such as a pancreatic adenocarcinoma (e.g. a pancreatic ductal adenocarcinoma).

The reference to "cancer cell" herein (e.g. in the context of the "ability to kill cancer cells") may refer to a cancer cell of any of above-mentioned cancers. Suitably the "cancer cell" may be a solid tumour cancer cell, such as a pancreatic cancer cell.

In one embodiment an in vitro cell culture of haematopoietic cells, an in vitro cell culture of granulocytes, or a pharmaceutical composition of the invention is administered to a subject (e.g. a subject with cancer). Prior to administration there may be a matching step between the medicament (e.g. comprising an in vitro cell culture of haematopoietic cells, an in vitro cell culture of granulocytes, or a pharmaceutical composition of the invention) and the subject to be treated. Matching may be based on data derived from the donor from which the haematopoietic cell, or granulocyte is derived, and similar data obtained from the subject to be treated. Matching may be achieved on the basis of blood group type, human leukocyte antigen (HLA) type similarity, or combinations thereof.

A typical treatment regimen may include administering from $10^6$, $10^7$, $10^8$ or $10^9$ cells to a subject, or up to $10^{12}$, $10^{13}$ or $10^{14}$ cells to a subject. In one embodiment a treatment regimen includes administering a dose of at least $1 \times 10^9$ cells to a subject. Suitably, a treatment regimen may include administering a dose of at least $2 \times 10^9$ cells or at least $5 \times 10^9$ cells to a subject. In one embodiment a treatment regimen may include administering a dose of at least $1 \times 10^{10}$ cells or at least $5 \times 10^{10}$ cells to a subject. At least $1 \times 10^{11}$ or at least $2 \times 10^{11}$ cells may be administered to a subject. In some embodiments between $1 \times 10^9$ to $3 \times 10^{11}$ or $1 \times 10^{10}$ to $3 \times 10^{11}$ cells are administered to a subject. Suitably, between $5 \times 10^{10}$ to $2.5 \times 10^{11}$ cells are administered to a subject.

A subject for treatment may be dosed once, twice, three times, four times, five times, or six times per week. Alternatively a subject may be dosed daily (e.g. once or twice daily). In other embodiments a subject may be dosed once weekly or bi-weekly. Preferably the dose is weekly. The skilled person will appreciate that the dose can be tailored based on the needs of the subject, and efficacy of the medicament. For example, where the medicament is highly efficacious, the dose may be lowered.

In one embodiment a subject for treatment is dosed weekly (e.g. once weekly) with at least $2 \times 10^9$ cells or at least $2 \times 10^{10}$ cells. Suitably, a subject for treatment may be dosed weekly with at least $1 \times 10^{11}$ or at least $2 \times 10^{11}$ cells.

The treatment term can be varied based on the response of the subject to the treatment, and/or the type and/or severity of the cancer. For example, the subject for treatment may be dosed for at least 1 or 2 weeks. Suitably the subject for treatment may be dosed for at least 3 or 4 weeks. In one embodiment the subject for treatment is dosed for at least 5 or 6 weeks, suitably at least 7 or 8 weeks.

In one embodiment a subject for treatment is dosed for 4-8 weeks with at least $2 \times 10^9$ cells, wherein said cells are administered once weekly. Suitably a subject for treatment is dosed for 8 weeks with at least $2 \times 10^9$ cells (preferably at least $2 \times 10^{10}$ or $2 \times 10^{11}$ cells), wherein said cells are administered once weekly.

Administration may be by any suitable technique or route, including but not limited to intravenous injection, intra-arterial injection, intraperitoneal injection, injection into a tumour resection cavity, intrathecal injection, or combinations thereof. Suitably the medicament may be administered intravenously.

A white blood cell growth factor may be administered with a medicament of the invention. The administration may be sequential or simultaneous (suitably simultaneous). Suitable white blood cell growth factors may include a granulocyte-macrophage colony-stimulating factor (GM-CSF), a granulocyte colony-stimulating factor (G-CSF), a growth hormone; serotonin, vitamin C, vitamin D, glutamine (Gln), arachidonic acid, AGE-albumin, an interleukin, TNF-alpha, Flt-3 ligand, thrombopoietin, foetal bovine serum (FBS), or combinations thereof. Suitably the white blood cell growth factors may comprise a granulocyte-macrophage colony-stimulating factor (GM-CSF), and a granulocyte colony-stimulating factor (G-CSF), and a growth hormone, and serotonin, and vitamin C, and vitamin D, and glutamine (Gln), and arachidonic acid, and AGE-albumin, and an interleukin, and TNF-alpha, and Flt-3 ligand, and thrombopoietin, and foetal bovine serum (FBS). Particular examples of the foregoing include but are not limited to LEUKINE® brand sargramostim, NEUPOGEN® brand filgrastim, and NEULAST A® brand 5 PEG-filgrastim.

Where the medicament is a haematopoietic cell (e.g. a haematopoietic cell culture) the medicament may be administered (e.g. sequentially or simultaneously, preferably simultaneously) with a granulocyte-colony stimulating factor; and a growth hormone; and a serotonin; and an interleukin. In one embodiment a granulocyte precursor cell (e.g. a granulocyte precursor cell culture) is administered (e.g. sequentially or simultaneously, preferably simultaneously) with a granulocyte-colony stimulating factor; and a growth hormone; and a serotonin; and an interleukin.

The present invention also provides a kit comprising an in vitro cell culture of haematopoietic cells, a granulocyte, an in vitro cell culture of granulocytes, or a pharmaceutical composition of the invention; and instructions for use of same in medicine. Suitably, the instructions may be for the use of the same in treating a cancer described in any one of the foregoing embodiments. In some embodiments the instructions also detail an appropriate dosage regimen (e.g. as described in a foregoing embodiment).

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

The headings provided herein are not limitations of the various aspects or embodiments of this disclosure.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a haematopoietic cell" includes a plurality of such candidate agents and reference to "the haematopoietic cell" includes reference to one or more haematopoietic cells and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The invention will now be described, by way of example only, with reference to the following Figures and Examples.

FIGURES

Embodiments of the invention will now be described, by way of example only, with reference to the accompanying Figures, in which.

EXAMPLES

Example 1

Recruitment of Donors

Figure 1:
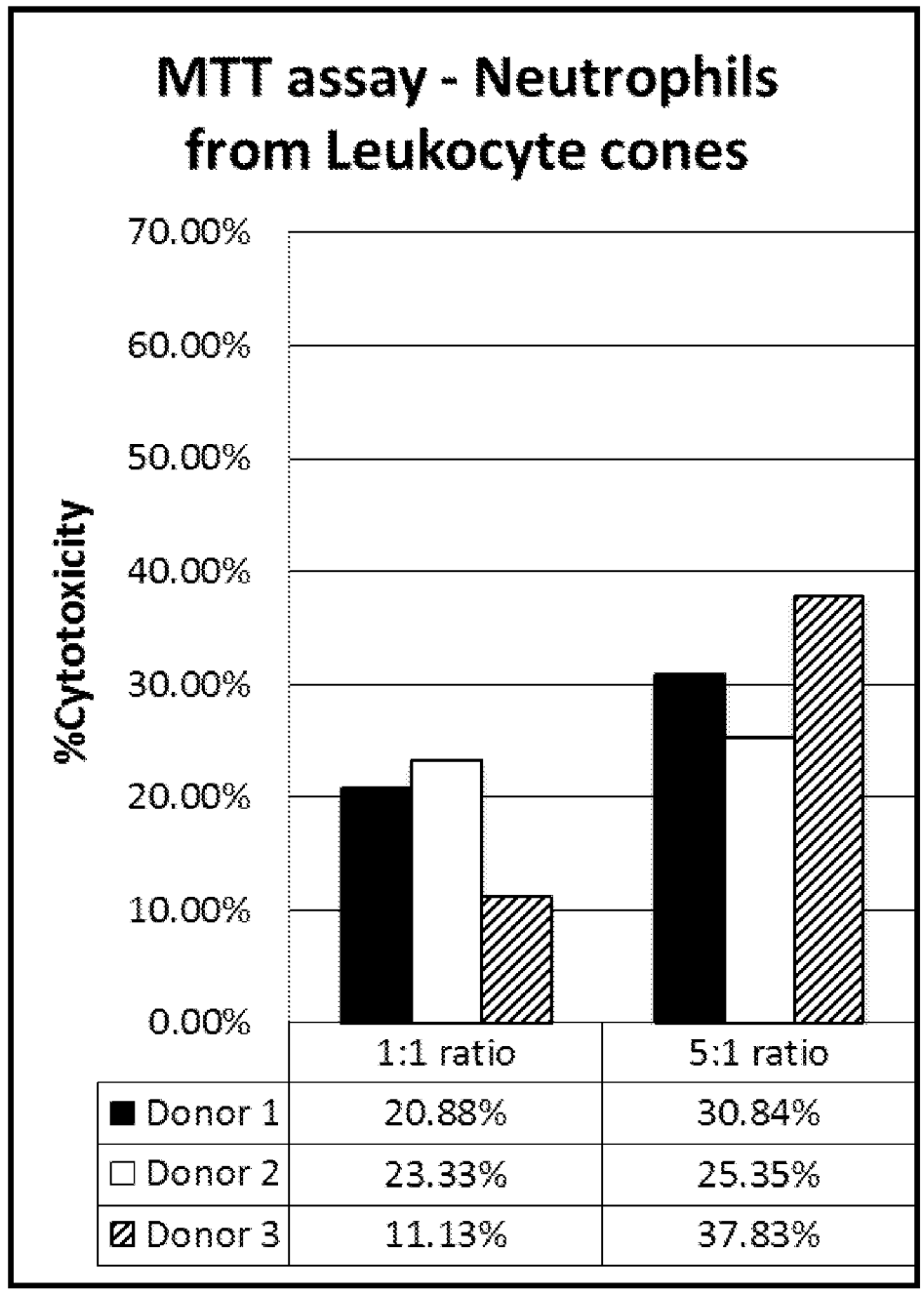
FIG. 1 shows cytotoxicity of different neutrophil donors and different effector to target cell ratios.

Donors are pre-selected based on the probability of having neutrophils exhibiting high levels of Cancer Killing Activity (CKA) in a CKA assay described in Example 2. Pre-selection criteria include:
  no serious medical or psychiatric condition that effecting provision of consent or sample collection;
  no personal or family history of the cancer(s) being targeted for therapy;
  no history of chemotherapy or radiation therapy within three months prior to the sampling date;
  aged 18-24;
  optionally male (without wishing to be bound by theory, neutrophils from males are believed to exhibit the highest levels of CKA when tested in the CKA assay); and
  optionally blood groups O or rhesus negative.

White Blood Cells (WBCs) are collected by drawing approximately 18 ml of human blood from a donor. The blood is split into three BD Vacutainer™ CPT tubes and centrifuged at 175×g for 35 minutes at 23° C. The mononuclear cell (MN) layer is collected and transferred to a 15 ml conical tube. The MN cells are centrifuged at 420×g for 5 minutes at 23° C., and washed with 10 ml Dulbecco's Modified Eagle's Medium (DMED) (Invitrogen, Carlsbad, CA)+10% foetal bovine serum (FBS) (Sigma. St. Louis, MO). Cells are counted and resuspended in medium to a final concentration of $1.6 \times 10^6$ cells/ml.

Example 2

Testing CKA of Extracted Granulocytes in a CKA Assay

Cells are cultured in DMEM+10% FBS in a T25 flask to 80% confluence. The cell line is grown and maintained at 37° C., 8% $CO_2$, in T75 $cm^2$ cell culture flasks in DMEM supplemented with the following ingredients: 10% volume/volume FBS, penicillin (Sigma. St. Louis, MO), streptomycin (Sigma. St. Louis, MO), and supplemental L-glutamine (Sigma. St. Louis, MO). Cultured pancreatic cancer cells (e.g. Capan-2, ATCC HTB-80; Panc 10.05, ATCC CRL-2547; CFPAC-1, ATCC CRL-1918; HPAF-II, ATCC CRL-1997; SW 1990, ATCC CRL-2172; BxPC-3, ATCC CRL-1687; AsPC-1, ATCC CRL-1682; ATCC® TCP-1026®; SW1990, ATCC CRL-2172; SU.86.86, ATCC CRL-1837; BXPC-3, ATCC CRL-1687; Panc 10.05, ATCC CRL-2547; MIA-PaCa-2, ATCC CRL-1420; PANC-1, ATCC CRL-1469; or ATCC® TCP-2060™ commercially available from the American Type Culture Collection—United Kingdom (U.K.), Guernsey, Ireland, Jersey and Liechtenstein, LGC Standards, Queens Road, Teddington, Middlesex TW11 OLY, UK) are split and passaged before reaching 70% surface confluence in culture flasks.

Cells are trypsinised, harvested and counted with Trypan Blue. Assay plates (24-well) are seeded with $8 \times 10^4$ pancreatic cancer cells (e.g. pancreatic ductal adenocarcinoma cells) per well in 24-well flat bottom plates. Plates are incubated at 37° C. in 5% $CO_2$ for 24 hours. Cells are labelled with 2.5 µM CellTracker™ Green for 45 minutes. Fresh medium is added to cells and they are returned to a $CO_2$-incubator.

The CKA assay is carried out by adding 500 µl of MN cell suspension ($8 \times 10^5$ granulocytes) to each well in which the pancreatic cancer cells are grown for 24 hours. The cells are mixed and placed in an incubator in 5% $CO_2$ for 24 hours at 39° C. After a 24-hour incubation, cells are harvested by trypsinisation and centrifuged. Cells are resuspended in 100 µl cold phosphate-buffered saline (PBS), and 125 µl 0.4% Trypan Blue subsequently added. Cells are counted under microscope (using phase contrast and fluorescence microscopy).

Granulocytes (e.g. neutrophils) capable of killing at least 70% or at least 80% of the cancer cells (i.e. having at least 70% CKA or 80% CKA, respectively) in the assay are considered particularly suitable for use in treating cancer.

Example 3

Testing Surface Potential of Haematopoietic Cells and Neutrophils

Electrophoresis is used to investigate the surface potential variation in haematopoietic cells (e.g. haematopoietic stem cells, and/or precursor cells) and neutrophils by measuring the electrophoretic mobility. The suspended cells are collected from culture, by mechanical detachment and collection from the culture substrate. Collected cells are redistributed in an electrophoresis buffer solution containing 10 mM Tris-HCl and 291 mM glucose, and are introduced into a rectangular glass electrophoresis chamber. 200V DC is applied across the electrophoresis chamber. The electrophoretic velocity of cells, u, is measured by recording the time needed for cells passing a fixed length with 3 mA under a microscope with a CCD camera. The electrophoretic mobility, p, is calculated by $\mu = ugS/I$, where g is the conductivity of medium, S is the cross-sectional area of the electrophoresis chamber, and I is the current. For each condition typically at least 9 readings are performed to calculate cell electrophoretic mobility.

Example 4

Extracting Haematopoietic Stem Cells from Peripheral Blood

Upon giving consent the donors are given a granulocyte-colony stimulating factor (G-CSF) and/or a granulocyte-macrophage colony-stimulating factor (GM-CSF), e.g. Neupogen® (commercially available from Amgen Inc. USA) to help harvest peripheral haematopoietic stem cells with minimal possible discomfort to donors. Cell surface polypeptide markers are used for identifying long-lasting multipotent stem-cells. Suitably markers may include $CD34^+$, $CD59^+$, $Thy1^+$, $CD38^{low/-}$, $C-kit^{-/low}$, and $lin^-$.

Example 5

Expansion and Differentiation of Haematopoietic Cells

The haematopoietic cells (e.g. haematopoietic stem cells) are stimulated using a supernatant growth factor suspension, to either develop more stem cells or differentiate into precursor cells (e.g. myeloid or granulocyte progenitor cells) or granulocytes. Suitable neutrophil synthesis methods are disclosed in Lieber et al, Blood, 2004 Feb. 1; 103(3):852-9, and Choi et al, Nat. Protoc., 2011 March; 6(3):296-313.

The protocol is composed of four major stages:

culturing and proliferation of haematopoietic cells;

short-term expansion of multipotent myeloid progenitors with a high dose of granulocyte-macrophage colony-stimulating factor (GM-CSF), a granulocyte colony-stimulating factor (G-CSF), a human growth hormone (HGH); serotonin, vitamin C, vitamin D, glutamine (Gln), arachidonic acid, AGE-albumin, interleukin-3 (IL-3), interleukin 8 (IL-8), Interleukin-4 (IL-4), Interleukin-6 (IL-6), interleukin-18 (IL-18), TNF-alpha, Flt-3 ligand, thrombopoietin, foetal bovine serum (FBS), or combinations thereof; and directed differentiation of myeloid progenitors into neutrophils, eosinophils, dendritic cells (DCs), Langerhans cells (LCs), macrophages and osteoclasts.

Example 6

Preparation of Cell Banks

Haematopoietic stem cells, granulocyte precursor cells and granulocytes obtainable therefrom, are cryogenically frozen and stored in appropriate cell banks.

Example 7

Use in Patients for Treating Solid Tumours

Stored haematopoietic cells (e.g. haematopoietic stem cells or granulocyte precursor cells obtainable therefrom), and granulocytes (e.g. neutrophils) differentiated therefrom are matched to cancer patients based on their cancer type, blood type (ABO, rhesus and HLA), and/or genetics. Patients may also be matched based on human leukocyte antigen (HLA) similarity.

Patients are treated using:

IV infusion of haematopoietic cells (including haematopoietic stem cells, and granulocyte precursor cells) together with granulocyte-colony stimulating factor, human growth hormone, serotonin, and interleukin into the patient; or IV infusion of stimulated granulocyte precursor cells (obtainable from haematopoietic stem cells) into the patient. Without wishing to be bound by theory, it is believed that said cells naturally differentiate into granulocytes (e.g. neutrophils) having a high CKA in a CKA assay in vivo; or direct IV infusion of granulocytes (e.g. neutrophils) having a high CKA in a CKA assay which have been differentiated from haematopoietic cells (e.g. haematopoietic stem cells).

Typically, cells are infused once weekly for 8 weeks with a cell volume of $2 \times 10^{11}$ administered per week. Progress of the therapy is monitored and dosing is adapted accordingly.

Example 8

Treatment of a Patient with Pancreatic Cancer

Mary is diagnosed with metastatic pancreatic ductal adenocarcinoma (PDAC) at age 69. Surgery is no longer an option (un-resectable), gemcitabine inadequate in preventing disease progression, and Abraxane or Folfirinox unsuitable on her Oncologist's recommendation due to the side-effects that will render her incapable of enjoying the time she has left with her family. Mary's prognosis is 3-6 months to live, and she is desperate to live long enough to see her newly-expected grandchild.

Mary is invited to try Leukocyte Infusion Therapy (LIFT). To assess the potential suitability of the therapy, the hospital extracts 20 ml of blood from Mary and sends it for analysis using the Cancer Killing Activity Assay, the assay identifies that the pancreatic cancer killing activity of her granulocytes is less than 5%. Such a low reading demonstrates the inadequacy of her own innate immune system to fight off her cancer which will kill her if the efficacy of the granulocytes in her body is not improved.

Mary's patient notes and assay result are used to find a suitable cancer killing granulocyte match. Mary is blood group A. Mary's profile is processed using a cell database for a cell bank and suitable granulocytes (that prior to cryogenic freezing exhibit a 70-90% Cancer Killing Activity (CKA) in the Cancer Killing Activity assay of Example 2) are identified. Cryogenically freezing granulocytes helps preserve the CKA and so the cells are able to be dispatched directly to the hospital (The Royal Marsden) with no further testing. Mary is due to visit that week for her first treatment. The hospital appropriately stores the cells. Mary receives her first infusion of $2 \times 10^9$ granulocytes having CKA on the $13^{th}$ December under close supervision. Mary is invited back to the hospital 3 days later where she is given an ultrasound scan which reveals significant tumour lysis and no signs of tumour lysis syndrome. The medical team decide to increase the granulocyte dose incrementally over 3 successive treatment sessions until it reaches $2 \times 10^{11}$.

An ultrasound is carried out on the $17^{th}$ January; one week after the 4-week course of four treatments is completed, and shows complete tumour destruction and conversion into scar tissue with good healing taking place. 20 ml of Mary's blood is taken: i) to assess the presence of metastatic cancer cells in her blood (to confirm complete clearance of the cancer) alongside a biopsy; and ii) to test the Cancer Killing Activity of Mary's granulocytes (to indicate risk of remission). Mary receives regular check-ups first monthly and then 6-monthly.

Two years later a new tumour is discovered on Mary's pancreas. Her clinicians treat the tumour with radiotherapy and administer a single high dose of LIFT to ensure destruction of any cancer cells that may be present in the blood. Mary enjoys the life that is given back to her and the family she gets to see grow up.

After the therapy, the haematopoietic cells (e.g. haematopoietic stem cells) from the cell bank are stimulated to produce more granulocytes (having desired CKA as tested using the assay of Example 2) to replenish stocks. Thus sufficient stock of the required granulocytes for similar patient situations is ensured.

Example 9

MTT "CKA Assay"

MTT (3-(4,5-dimethylthiazol-2-yl)-2,5-diphenyltetrazolium bromide), a yellow tetrazole which is positively charged and readily penetrates viable eukaryotic cells. Viable cells with active metabolism convert MTT into a purple coloured formazan product (1(E,Z)-5-(4,5-dimethylthiazol-2-yl)-1,3-diphenylformazan) through NAD(P)H-dependent oxidoreductase mitochondrial enzymes, with an absorbance maximum near 570 nm. When cells die, they lose the ability to convert MTT into formazan, thus colour formation serves as a useful and convenient marker of only the viable cells. A solubilization solution is added to dissolve the insoluble purple formazan product into a coloured solution. The absorbance of this coloured solution can be quantified by measuring at wavelength 570 nm by a spectrophotometer. The absorption of a reference wavelength of 690 nm is subtracted from the absorption of the 570 nm wavelength. Therefore, the MTT assay was used to measure how many live cells remained as a way to determine Cancer Killing Activity (CKA)—cytotoxicity to cancer cells.

Method for Preparing Hela Target Cells

Day 1:
1) HeLa cells (a robust type of cervical cancer cell) were cultured and harvested when they reached log phase
2) 10000 HeLa cells (target cells) were added to each well of a 96 Flat bottom plate at a final volume of 100 uL
3) Target cells were left to adhere overnight before leukocyte (effector cells) addition and all experimental conditions were set in triplicates Day 2:
4) Effector cells were added to the target cells at different ratios (e.g. 1:1, 5:1, 10:1, 50:1, effector to target cells)
5) The cells were left to incubate for 16-24 hours at 37° C.
6) Target cells alone and target cells in the presence of Triton X were also plated in triplicates as controls for 0% and 100% cytotoxicity, respectively.

After the Desired Incubation Time:
1) The wells were washed with PBS twice to remove effector cells and dead target cells
2) MTT solution was prepared by dissolving the kit solution 10 times with culture medium, i.e: for 100 wells: take 1000 uL (1 mL) of MTT stock (provided in the kit) and 9000 uL (9 mLs) of culture medium (RPMI-1640) added
3) Add 100 ul/well of the prepared MTT solution at step 2
4) This was incubated for 4 h
5) MTT Solution was removed from all wells and 100 ul/well of the solvent was added (provided in the kit).
6) The formazan crystals were solubized when needed by pipetting and the plate read at 570 and 690 nm. Background absorbance measured at 690 nm was subtracted from absorbance measured at 570 nm.

Demonstrating Variable CKA in Donor Neutrophils

Leukocyte cones from anonymous blood donors were selected and neutrophils were isolated by Ficoll-Hypaque separation (Oh H, Siano B, Diamond S. Neutrophil Isolation Protocol. Journal of Visualized Experiments: JoVE. 2008; (17):745). These neutrophils were used in the aforementioned MTT assay in ratios of effector to target cell of 1:1, and 5:1.

FIG. 1 shows the percentage cytotoxicity recorded by MTT for the different donors. There is a difference between the donors at ratios 1:1 and 5:1. In conclusion, the MTT assay, is able to demonstrate differences in CKA between neutrophils from different donors.

Example 10

Demonstrating CKA of Stem Cell Derived Neutrophils

Culturing Neutrophils from CD34+ Stem Cells

We cultured neutrophils from umbilical cord blood derived stem cells expressing the CD34 protein, using the protocol as described by Timmins N E, Palfreyman E, Marturana F, Dietmair S, Luikenga S, Lopez G, et al. Clinical scale ex vivo manufacture of neutrophils from hematopoietic progenitor cells. Biotechnology and bioengineering. 2009; 104(4):832-40.

The resulting cultures were tested for neutrophil content using CD11b+ and CD15 markers by Fluorescence-activated cell sorting (FACS). We also measured the production of Reactive Oxygen Specimens (ROS), more specifically the production of superoxide anion ($O_2-$) by use of the nitroblue tetrazolium (NBT) assay (kit and protocol commercially-available from Sigma-Aldrich, Catalogue No. 840W-1KT).

Since differences in ROS activity were found based on the age of the stem cell derived neutrophils (data not shown), we enumerated three stem cell batches on the same day for consistency/comparability. The results of the FACS derived counting of the proportion of CD11b+ and CD15+ cells are listed in Table 1.

TABLE 1

Percentage of CD11b+/CD15+ positive neutrophils

| FACS on 26.09.2017 | CD11b+ CD15+ (% of all cells) | CD34+ (% of all cells) |
|---|---|---|
| CD34+ 14.09.2017 batch 008A (12 days in culture) | 77.8 | 4.45 |
| CD34+ 14.09.2017 batch 709A (12 days in culture) | 76.0 | 5.1 |
| CD34+ 14.09.2017 915 (12 days in culture) | 69.2 | 10.0 |

Demonstrating CKA of CD34+ Derived Neutrophils

Figure 2:
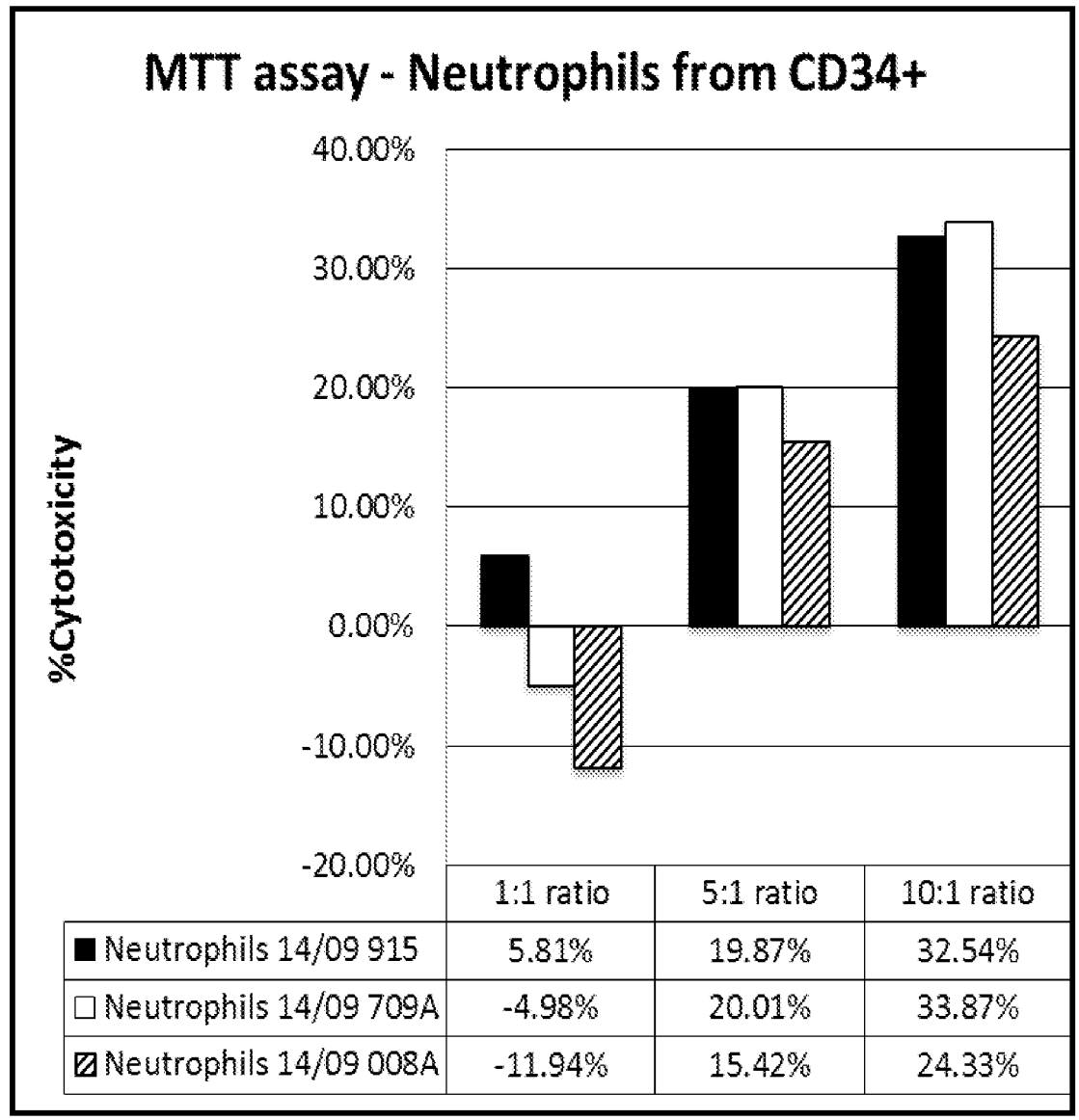
FIG. 2 shows cytotoxicity results of three CD34+ stem cell derived neutrophil populations from different donors.

Stem cell derived neutrophils (batches 008A, 709A and 915) were used as effector cells in the CKA MTT assay using HeLa target cells (see Example 9). The effector to target cell ratio is based on CD11b+/CD15+. The results are summarized in FIG. 2, which demonstrate that CD34+ stem cell derived neutrophils demonstrate cytotoxicity in a HeLa cell CKA assay and that the results are different between different donors. Batch 008A shows consistently lower cytotoxicity than batches 915 and 709A up to 10:1 effector to target ratio, despite being prepared at the same time as the other batches and cultured in the same way.

The results demonstrate that stem cells from different donors can a) be differentiated in vitro to produce neutrophils that demonstrate cancer killing abilities, and b) that this cancer killing activity varies by the source donor.

The results support the fact that the cancer killing activity (CKA) by the innate immune system varies by individual and that the same innate variance in CKA seen in neutrophils taken directly from donors via leukocyte cones, is also shown in a donor's stem cells. By selecting donors with proven high cancer killing activity of their innate immune system, and using their haematopoietic cells (i.e. haematopoietic stem cells) for ex vivo expansion and differentiation, a cell bank can be created with leukocytes with high cancer killing activity to be used in the treatment of cancer.

Example 11

Isolation of High-Density Neutrophils 10 ml of heparinized (20 U/ml) human blood is mixed with an equal volume of 3% Dextran T500 in saline and incubated for 30 minutes at room temperature to sediment erythrocytes. A 50 ml conical polypropylene tube is prepared with 10 ml sucrose 1.077 g/ml and slowly layered with a leukocyte-rich supernatant on top of the 1.077 g/ml sucrose layer prior to centrifuging at 400×g for 30 minutes at room temperature without brake. The high-density neutrophils (HDN) appear in the pellet. Low-density neutrophils (LDN) co-purify with monocytes and lymphocytes at the interface between the 1.077 g/ml sucrose layer and plasma.

The HDNs may be tested in a CKA assay described herein. Haematopoietic cells are suitably obtained from a donor having HDNs.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method of treating cancer in a subject in need thereof comprising administering a formulation to the subject in need thereof thereby treating cancer in the subject in need thereof, wherein the formulation comprises hematopoietic cells derived from a donor that produces granulocytes with the ability to kill cancer cells.

2. The method of claim 1, wherein the cancer comprises a solid tumor cancer.

3. The method of claim 1, wherein the cancer comprises pancreatic cancer, liver cancer, oesophageal cancer, stomach cancer, cervical cancer, ovarian cancer, lung cancer, bladder cancer, kidney cancer, brain cancer, prostate cancer, myeloma cancer, non-Hodgkin's lymphoma (NHL), larynx cancer, uterine cancer, or breast cancer.

4. The method of claim 1, wherein the granulocytes comprise neutrophils.

5. The method of claim 1, wherein the hematopoietic cells comprise hematopoietic stem cells or granulocyte precursor cells.

6. The method of claim 5, wherein the granulocyte precursor cells comprise common myeloid progenitor cells, myeloblasts, Neutrophilic promyelocytes, Neutrophilic myelocytes, Neutrophilic metamyelocytes, Neutrophilic Band cells, or combinations thereof.

7. The method of claim 1, wherein:
the granulocytes with the ability to kill cancer cells have a positively charged cell surface; and/or
the granulocytes with the ability to kill cancer cells have a density of at least 1.077 g/ml.

8. The method of claim 1, wherein the donor produces granulocytes which kill at least 5% of cancer cells in a cancer killing assay.

9. The method of claim 8, wherein the cancer killing assay comprises:
a) admixing granulocytes obtained from the donor with a cancer cell line to form an admixture;

b) incubating the admixture; and c) measuring the percent (%) of cancer cells killed in the incubated admixture.

10. The method of claim 1, wherein the donor is a human donor.

11. The method of claim 1, wherein the donor is an 18-25 year old human male.

12. The method of claim 1, wherein the formulation further comprises a carrier, optionally wherein the carrier comprises a pharmaceutically-acceptable carrier, tumor necrosis factor alpha (TNFα), a granulocyte-macrophage colony-stimulating factor (GM-CSF), a granulocyte colony-stimulating factor (G-CSF), a growth hormone; serotonin, vitamin C, vitamin D, glutamine (Gln), arachidonic acid, advanced glycation end-product (AGE)-albumin, an interleukin, Flt-3 ligand, thrombopoietin, fetal bovine serum (FBS), or combinations thereof.

13. A method of treating cancer in a subject in need thereof comprising administering a formulation to the subject in need thereof thereby treating cancer in the subject in need thereof, wherein the formulation comprises granulocytes, granulocyte precursor cells, or combinations thereof wherein the granulocytes, granulocyte precursor cells, or combinations thereof are differentiated ex vivo from hematopoietic cells derived from a donor that produces granulocytes with the ability to kill cancer cells.

14. The method of claim 13, wherein the cancer comprises a solid tumor cancer.

15. The method of claim 13, wherein the cancer comprises pancreatic cancer, liver cancer, oesophageal cancer, stomach cancer, cervical cancer, ovarian cancer, lung cancer, bladder cancer, kidney cancer, brain cancer, prostate cancer, myeloma cancer, non-Hodgkin's lymphoma (NHL), larynx cancer, uterine cancer, or breast cancer.

16. The method of claim 13, wherein the granulocytes comprise neutrophils.

17. The method of claim 13, wherein the granulocyte precursor cells comprise common myeloid progenitor cells, myeloblasts, Neutrophilic promyelocytes, Neutrophilic myelocytes, Neutrophilic metamyelocytes, Neutrophilic Band cells, or combinations thereof.

18. The method of claim 13, wherein the formulation further comprises a carrier, optionally wherein the carrier comprises a pharmaceutically-acceptable carrier, tumor necrosis factor alpha (TNFα), a granulocyte-macrophage colony-stimulating factor (GM-CSF), a granulocyte colony-stimulating factor (G-CSF), a growth hormone; serotonin, vitamin C, vitamin D, glutamine (Gln), arachidonic acid, advanced glycation end-product (AGE)-albumin, an interleukin, Flt-3 ligand, thrombopoietin, fetal bovine serum (FBS), or combinations thereof.

* * * * *